United States Patent
Eto et al.

(10) Patent No.: US 11,952,587 B2
(45) Date of Patent: Apr. 9, 2024

(54) METHOD FOR PRODUCING PLATELETS

(71) Applicants: KYOTO UNIVERSITY, Kyoto (JP); MEGAKARYON CORPORATION, Kyoto (JP)

(72) Inventors: Koji Eto, Kyoto (JP); Sou Nakamura, Kyoto (JP); Yukitaka Ito, Kyoto (JP)

(73) Assignees: KYOTO UNIVERSITY, Kyoto (JP); MEGAKARYON CORPORATION, Kyoto (JP)

( * ) Notice: Subject to any disclaimer, the term of this patent is extended or adjusted under 35 U.S.C. 154(b) by 1251 days.

(21) Appl. No.: 16/491,219

(22) PCT Filed: Mar. 5, 2018

(86) PCT No.: PCT/JP2018/008279
§ 371 (c)(1),
(2) Date: Jan. 15, 2020

(87) PCT Pub. No.: WO2018/164040
PCT Pub. Date: Sep. 13, 2018

(65) Prior Publication Data
US 2020/0216807 A1    Jul. 9, 2020

(30) Foreign Application Priority Data

Mar. 6, 2017 (JP) ................ 2017-042033
Apr. 28, 2017 (JP) ................ 2017-089855

(51) Int. Cl.
C12N 5/078 (2010.01)
C12N 15/85 (2006.01)

(52) U.S. Cl.
CPC ........... *C12N 5/0644* (2013.01); *C12N 15/85* (2013.01); *C12N 2501/105* (2013.01); *C12N 2506/02* (2013.01)

(58) Field of Classification Search
None
See application file for complete search history.

(56) References Cited

U.S. PATENT DOCUMENTS

2014/0127815 A1    5/2014   Eto et al.
2016/0002586 A1    1/2016   Mitchell

FOREIGN PATENT DOCUMENTS

| EP | 2708597 A1 | 3/2014 |
|---|---|---|
| EP | 3372674 A1 | 9/2018 |
| WO | 2012/157586 | 11/2012 |
| WO | 2014/123242 | 8/2014 |
| WO | 2015/174443 | 11/2015 |
| WO | 2016/129593 | 8/2016 |
| WO | 2016/204256 | 12/2016 |

OTHER PUBLICATIONS

Jiang et al., Blood, Sep. 25, 2014, 124(13)2094-2103 (Year: 2014).*
Chatterjee, Madhumita, et al. "Macrophage migration inhibitory factor limits activation-induced apoptosis of platelets via CXCR7-dependent Akt signaling." Circulation research 115.11: 939-949. (Year: 2014).*
Ito, Yukitaka, et al. "High-Vorticity with Periodic Flow Enhances in Vitro Biogenesis of Healthy Platelets from iPSC-Derived-Megakaryocytes." Blood 128.22: 2181. (Year: 2016).*
Extended European Search Report corresponding to Ep 18763555.2; dated Nov. 9, 2020 (10 pages).
Nakamura, Sou , et al., "Expandable Megakaryocyte Cell Lines Enable Clinically Applicable Generation of Platelets from Human Induced Pluripotent Stem Cells", Cell Stem Cell, 14, 2014, 535-548.
Nakagawa et al. "Two differential flows in a bioreactor promoted platelet generation from human pluripotent stem cell-derived megakaryocytes" Exp. Hema tol., 41(8): 742-748 (2013).
International Search Report and Written Opinion corresponding to PCT/JP2018/0082791, dated Jun. 5, 2018 (6 pp).
Machlus et al. "CCL5 derived from platelets increases megakaryocyte proplatelet formation" Blood, 127(7):921-926 (2016).
Junt et al. "Dynamic Visualization of Thrombopoiesis Within Bone Marrow" Science, 317(5845): 1767-1770 (2007).
Japanese Office Action corresponding to JP 2019-504562; dated Apr. 18, 2022 (10 pages, including English translation).
Aslan, Joseph E., et al., "Histone deacetylase 6-mediated deacetylation of α-tubulin coordinates cytoskeletal and signaling events during platelet activation", American Journal of Physiology—Cell Physiology, 305(12), 2013, C1230-C1239.
Chatterjee, Madhumita , et al., "Macrophage migration inhibitory factor limits activation-induced apoptosis of platelets via CXCR7-dependent Akt signaling", Circulation Research, 115(11), 2014, 939-949.

* cited by examiner

Primary Examiner — Arthur S Leonard
Assistant Examiner — Josephine M Gonzales
(74) Attorney, Agent, or Firm — Myers Bigel, P.A.

(57) ABSTRACT

Healthy functional platelets are mass produced. A method for producing platelets, comprising: (1) a culture step of culturing megakaryocytes in a platelet producing medium in the presence of mechanical stress and platelet production promoting factors including MIF, NRDc, IGFBP2, TSP-1, PAI-1, and CCL5, and (2) a harvest step of harvesting the platelets obtained by the culture step; wherein the culture step comprises: (a) a step of promoting a release of the platelet production promoting factors from megakaryocytes by mechanical stress; and/or (b) a step of externally adding platelet production promoting factors including MIF, NRDc, and IGFBP2.

8 Claims, 32 Drawing Sheets

FIG.17
(a)
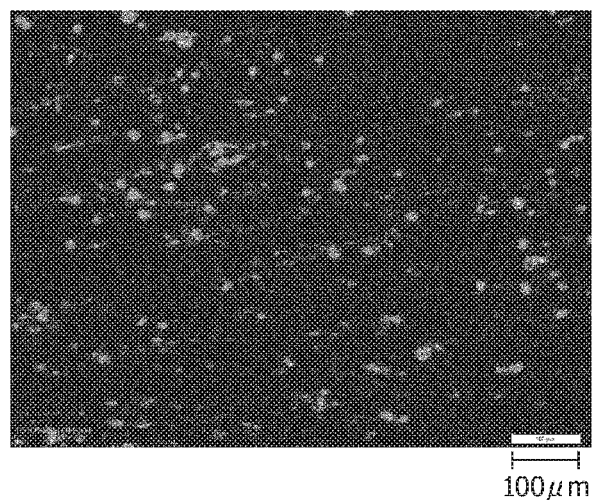
(b)
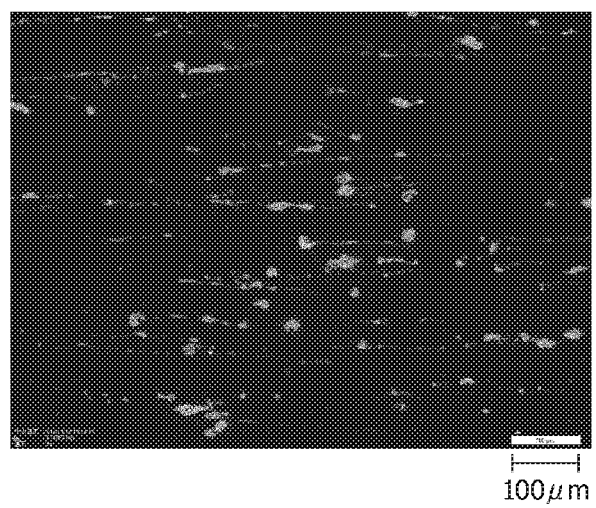
(c)
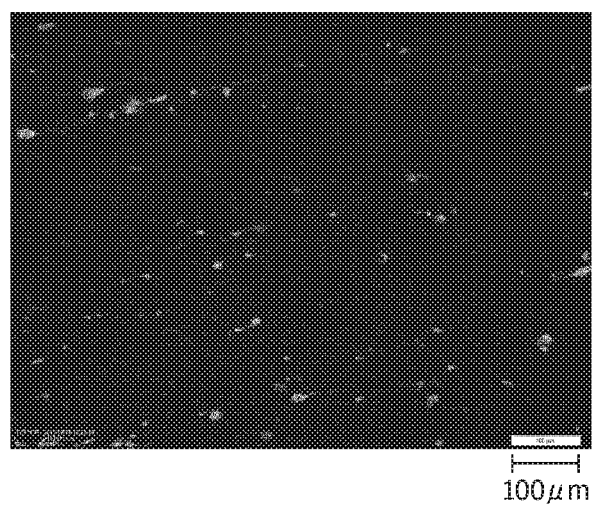

FIG.22
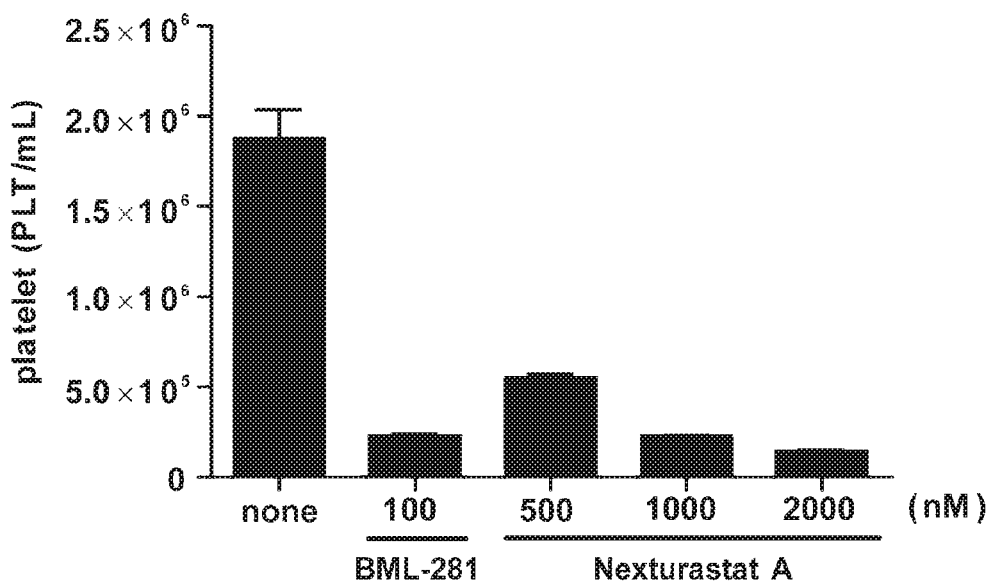
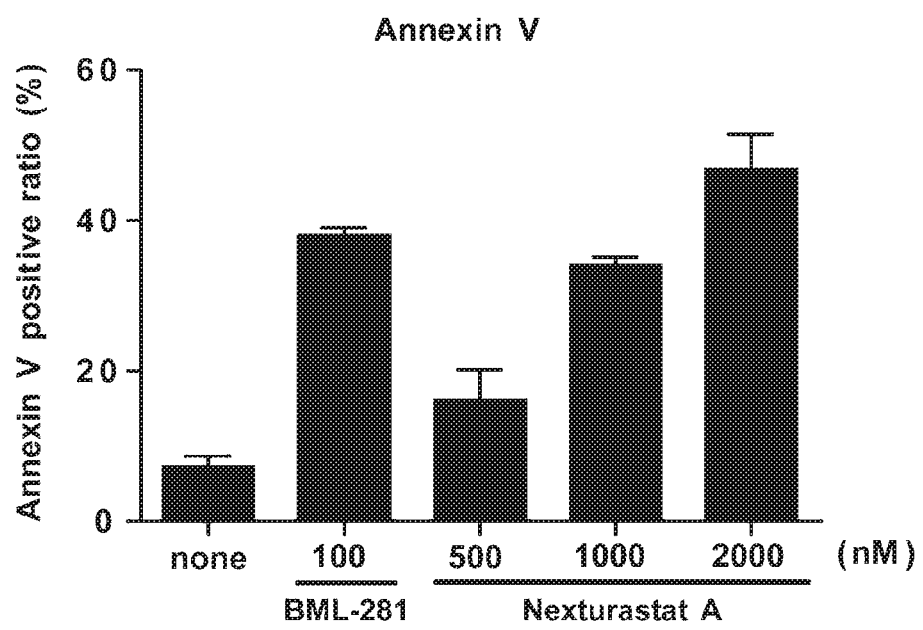

FIG.23
(a)
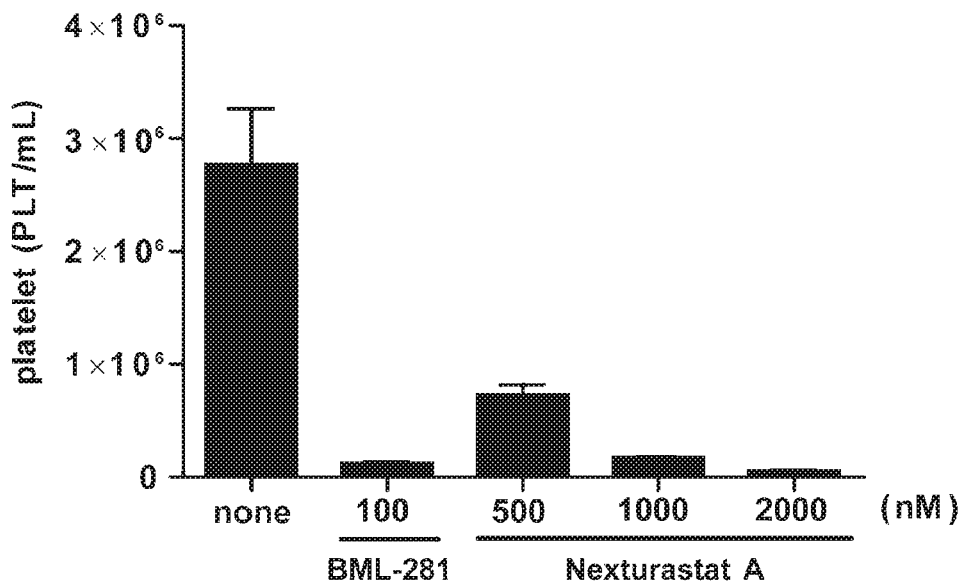
(b)
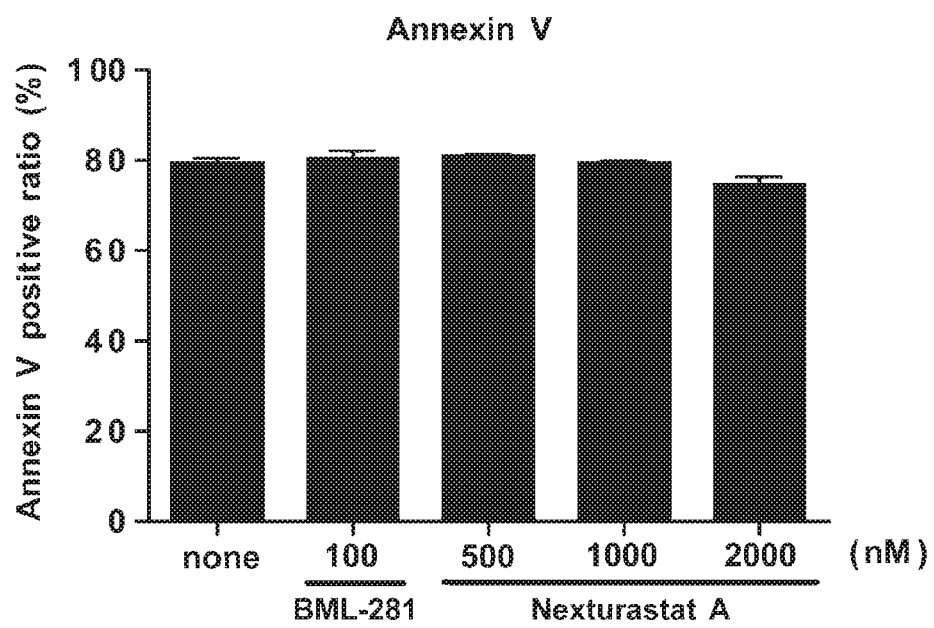

METHOD FOR PRODUCING PLATELETS

TECHNICAL FIELD

The present invention relates to a method for producing platelets and to a platelet production promoting agent that can be used in the method.

BACKGROUND ART

A platelet preparation is administered to patients for the purpose of treating and preventing massive bleeding at the time of surgery or injury or to those susceptible to bleeding associated with thrombocytopenia after anticancer drug therapy. At present, the production of platelet preparation relies on blood donation; however, there is a need for a safer and stable supply of platelets. To meet these needs, a method for producing platelets in vitro from megakaryocytes is developed. The present applicants have achieved methods for establishing immortalized megakaryocyte progenitor cell lines (imMKCL) by immortalizing a pluripotent stem cell as a source (e.g., see Patent Literature 1).

Mechanisms of producing platelets from megakaryocytes is widely studied. Based on the studies, it is suggested that platelet shedding is promoted by a flow-dependent shear force (e.g., see Non Patent Literature 1). Additionally, it is reported that chemokine CCL5 promotes platelet production from megakaryocytes (e.g. see Non Patent Literature 2).

CITATION LIST

Patent Literature

Patent Literature 1: International Publication No. WO2012/157586

Non Patent Literature

Non Patent Literature 1: Science 317 (5845), 1767-1770
Non Patent Literature 2: Blood, 2016; 127(7): 921-926

SUMMARY OF INVENTION

Technical Problem

Immortalized megakaryocyte progenitor cell lines have many advantages—it can be cryopreserved and can be induced to undergo multinucleation. Using such immortalized megakaryocyte progenitor cell lines, more efficient methods for on-demand, large scale production of stable platelets is desired.

Solution to Problem

For mass production of platelets, both megakaryopoiesis and platelet shedding approaches should be considered. For example, megakaryopoiesis can be improved by increasing the number of source cells, and the method for producing immortalized megakaryocytes developed by the present inventors (Patent Literature 1). On the other hand, it is suggested that platelet shedding is promoted by shear force (Non Patent Literature 1). During in vivo platelet production, IL-1 alpha induced acute platelet production and steady platelet production is observed. During acute platelet production, large amounts of platelets are produced in a short time, but the produced platelets have a high Annexin V positive ratio and have short circulation time in vivo. More specifically, the platelets produced by such a mechanism are not suitable for the use as a blood preparation. The present inventors paid attention to the mechanism of steady platelet production and have identified the factors which promote platelet production. The present inventors have found that during maturation phase, megakaryocytes promote the release of platelet production promoting factors when predetermined mechanical stress is applied or when platelet production promoting factors are supplemented, an increase in the amount of production of healthy platelets suitable for blood transfusion is obtained. The present invention is based on these observations.

More specifically, the present invention describes the features listed below.

[1] A method for producing platelets, comprising: (1) a culture step of culturing megakaryocytes in a platelet producing medium in the presence of mechanical stress and platelet production promoting factors including MIF, NRDc, IGFBP2, TSP-1, PAI-1, and CCL5, and (2) a harvest step of harvesting the platelets obtained by the culture step;
wherein the culture step comprises:
(a) a step of promoting a release of the platelet production promoting factors from megakaryocytes by mechanical stress; and/or
(b) a step of externally adding platelet production promoting factors including MIF, NRDc, and IGFBP2.

[2] The method according to [1], wherein the culture step comprises (a) a step for promoting the release of the platelet production promoting factors from megakaryocytes by mechanical stress.

[3] The method according to [1], wherein the culture step comprises (b) a step of externally adding platelet production promoting factors including MIF, NRDc, and IGFBP2.

[4] The method according to [3], wherein the platelet production promoting factors externally added further includes TSP-1, PAI-1, and CCL5.

[5] The method according to [3] or [4], wherein the platelet production promoting factors externally added are gene recombinants.

[6] The method according to any one of [3] to [5], wherein the step (b) of externally adding platelet production promoting factors is carried out 1 to 3 days before the harvest step.

[7] The method according to any one of [1] to [6], comprising a step of controlling an activity of histone deacetylase 6 in the culture step.

[8] The method according to any one of [1] to [7], comprising, before the step (1), a step of forcibly expressing an oncogene, a polycomb gene, and an apoptosis suppressor gene in cells more undifferentiated than megakaryocytes to obtain immortalized megakaryocytes.

[9] A platelet production promoting agent comprising a platelet production promoting factors containing MIF, NRDc, and IGFBP2.

[10] The platelet production promoting agent according to [9], wherein the platelet production promoting factors further contain TSP-1, PAI-1, and CCL5.

[11] The platelet production promoting agent according to [9] or [10], wherein the platelet production promoting factors are gene recombinants.

Advantageous Effects of Invention

According to the present invention, when megakaryocytes in the maturation phase are exposed to mechanical stress to promote the secretion of platelet production promoting agent and/or a platelet production promoting agent is externally added to promote the platelet production from megakaryocytes, the amount of platelets produced can be increased. Additionally, the platelets produced by the method of the present invention have a low Annexin V level and has characteristics suitable for the use as a blood preparation, and hence, extremely useful for the production of blood preparations.

BRIEF DESCRIPTION OF DRAWINGS

FIG. 6 explains that significant increase of the number of platelets was shown by shaking flask culture in which a Day 6 medium supernatant of VerMES shaking culture was added.

FIG. 17 is a set of representative fluorescence microscope image showing the platelet productions on the position X of bioreactor chip described in FIG. 13. FIG. 17, panel (a) is a representative photograph showing medium containing six factors, 6 factors—(minus) thrombospondin, and 6 factors—PAI-1. FIG. 17, panel (a) shows that platelets are produced when platelets are sheared off from PPF. FIG. 17, panel (b) is a representative photograph showing 6 factors—NRDc and shows that the shear of PPF is not carried out as desired. FIG. 17, panel (c) is a representative photograph showing each medium of control medium, 6 factors—MIF, and 6 factors—IGFBP2. FIG. 17, panel (c) shows that a platelet production site is not formed and that PPF cannot be achieved.

FIG. 19, panel (a) is a graph showing the results of CD41a/CD42b-positive platelets count, FIG. 19, panel (b) is a graph showing the number of platelets produced under each culture condition in terms of ratios when the number of platelets produced using a medium of the basic composition (none) is 1, and shows that a platelet yield is enhanced to about 1.2 times when six factors are added to the medium of the basic composition after 3 days (Day 3) after starting off culture. The results of PAC-1/CD62P-positive platelets counts are shown in FIG. 19, panel (c) for the medium with basic composition (none) and FIG. 19, panel (d) for 6 F Day 3. The results indicate that there is no problem in platelet functions.

FIG. 22 is a set of drawings showing the impact of adding HDAC6 inhibitors-BML-281 and Nexturastat A, to gene off imMKCL in a shaking flask culture (Flask). FIG. 22, panel (a) is a graph showing the number of platelets on Day 6 after the addition of HDAC6 inhibitors, and FIG. 22, panel (b) is a graph showing Annexin V positive ratios of the platelets obtained.

FIG. 23 is a set of drawings showing the impact of adding HDAC6 inhibitors-BML-281 and Nexturastat A, when a gene off imMKCL was subjected to static culture (Dish). FIG. 23, panel (a) is a graph showing the number of platelets on Day 6 after the addition of the HDAC6 inhibitors, and FIG. 23, panel (b) is a graph showing Annexin V positive ratios of the platelets released.

FIG. 24, panel (a) shows the cell morphology on Day 3 from the gene off in static culture to which DMSO was added; FIG. 24, panel (b) shows static culture to which 100 nM of BML-281 was added; and FIG. 24, panel (c) shows static culture to which 2 μM of Nexturastat A was added. Cell morphology on Day 6 from the gene off is shown in FIG. 24, panel (d) in static culture to which DMSO was added; FIG. 24, panel (e) in static culture to which 100 nM of BML-281 was added; and FIG. 24, panel (f) in static culture to which 2 μM of Nexturastat A was added.

FIG. 29, panel (a) shows a graph of type IV collagen (co14), FIG. 29, panel (b) shows a graph of vWF, FIG. 29, panel (c) shows a graph of vitronectin, FIG. 29, panel (d) shows a graph of fibrinogen, FIG. 29, panel (e) shows a graph of fibronectin, and FIG. 29, panel (f) shows a graph of vCAM1.

FIG. 30, panel (a) is the fluorescence microscope photograph of the cells on Day 1, FIG. 30, panel (b) is a fluorescence microscope photograph of the cells on Day 4, and FIG. 30, panel (c) is a fluorescence microscope photograph of the cells on Day 5.

DETAILED DESCRIPTION OF THE INVENTION

Figure 1:
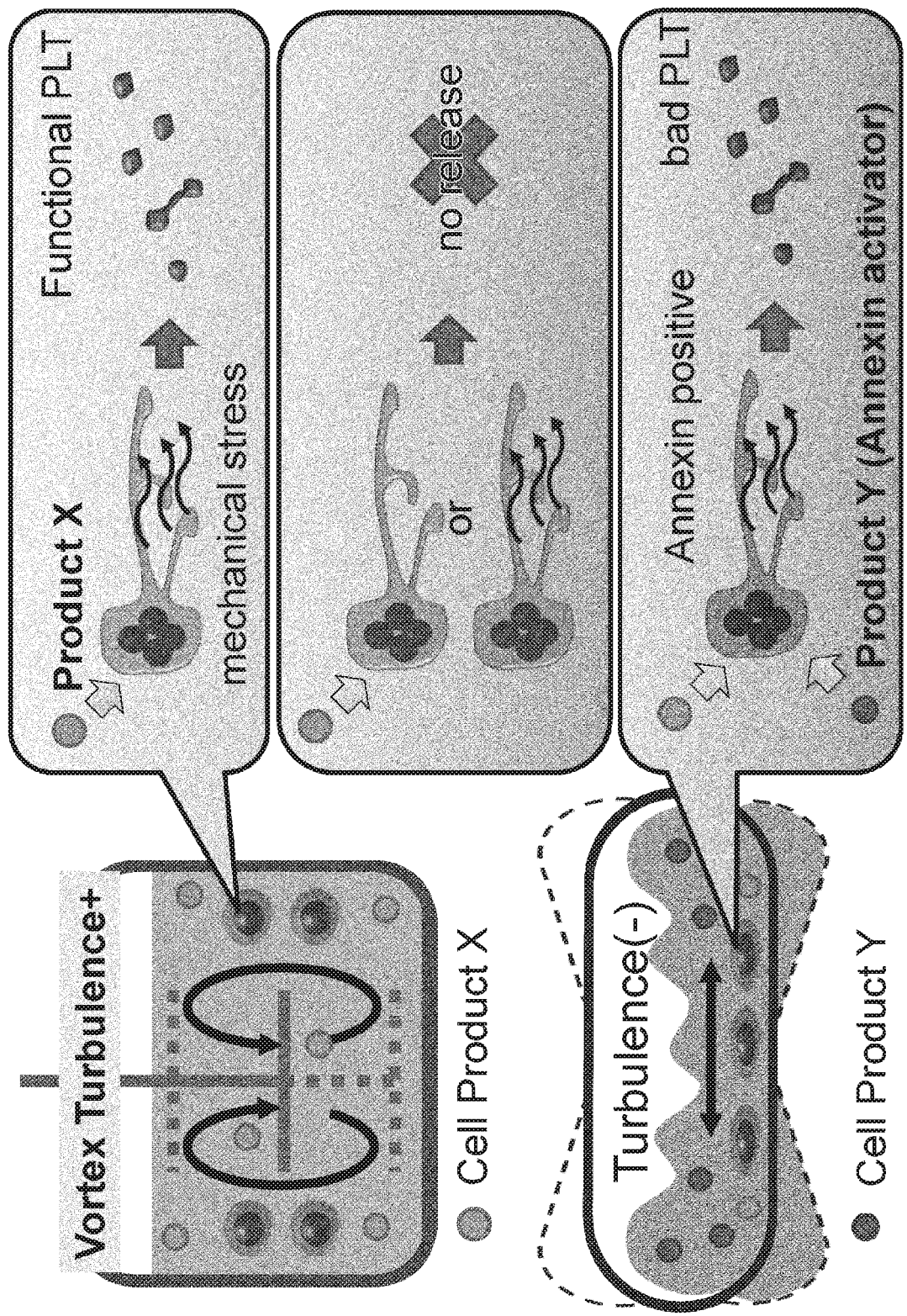
FIG. 1 is a conceptual drawing schematically showing mechanical stress and platelet production promoting factors in the method for producing platelets according to the present invention.

The present invention will now be described in detail in reference to the embodiments. However, the present invention is not limited to the following embodiments.

[Method for Producing Platelets]

The present invention, according to an embodiment, relates to a method for producing platelets, comprising: (1) a culture step of culturing megakaryocytes in a platelet producing medium in the presence of mechanical stress and platelet production promoting factors including macrophage migration inhibitory factor (MIF), nardilysin (N-arginine dibasic convertase; NRDc, also called NRD1 protein), insulin-like growth factor binding protein 2 (IGFBP2), thrombospondin 1 (TSP-1), plasminogen activation inhibitor (PAI-1), CCL5 (RANTES: regulated on activation, normal T cell expressed and secreted), and (2) a harvest step of harvesting the platelets obtained by the culture step;
in which the culture step comprises:
(a) a step of promoting a release of platelet production promoting factors from megakaryocytes by mechanical stress; and/or
(b) a step of externally adding platelet production promoting factors including MIF, NRDc, and IGFBP2.

In the method for producing platelets based on the present invention, the megakaryocyte subjected to the culture in the culture step (1) refers to the megakaryocyte defined as below. "Megakaryocyte" is the largest cell present in the bone marrow in vivo and has a characteristic of releasing platelets. Further, megakaryocyte is characterized by the presence of cell surface markers CD41a, CD42a, and CD42b, and may further express other markers selected from the group consisting of CD9, CD61, CD62p, CD42c, CD42d, CD49f, CD51, CD110, CD123, CD131, and CD203c. "Megakaryocyte," when multinucleated (polyploidized), has 16 to 32 times as many genomes as normal cells but, in the present specification, when simply referred to as "megakaryocyte," multinucleated megakaryocyte and megakaryocyte before multinucleation are both included as long as it has the above characteristics. The "megakaryocyte before multinucleation" has the same definition as "immature megakaryocyte" or "megakaryocyte in proliferation phase." Megakaryocyte can be obtained by various known methods and may be those obtained from any origin by any method without being particularly limited.

The method for producing platelets according to the present invention preferably comprises, before the culture step (1), a step of forcibly expressing an oncogene, a polycomb gene, and an apoptosis suppressor gene in cells more undifferentiated than megakaryocytes to obtain immortalized megakaryocytes.

A non-limiting example of a method for producing such an immortalized megakaryocyte is the method described in International Publication No. WO2011/034073. In this method, an indefinitely-proliferating immortalized megakaryocyte cell line can be obtained when an oncogene and a polycomb gene are forcibly expressed in the "cells more undifferentiated than megakaryocytes." Further, an immortalized megakaryocyte cell line can be obtained also by forcibly expressing an apoptosis suppressor gene in the "cells more undifferentiated than megakaryocytes" in accordance with the method described in International Publication No. WO2012/157586. These immortalized megakaryocyte cell lines, when the forced gene expression is terminated, proceed to multinucleation and start releasing platelets. Thus, the culture step (1) in the present invention can also be referred to a step of culturing by termination of the forced gene expression.

In the step to obtain immortalized megakaryocytes which can be carried out before the culture step (1), the methods described in the above literatures may be combined to obtain megakaryocytes. In such a case, the forced expression of an oncogene, a polycomb gene, and an apoptosis suppressor gene may be carried out simultaneously or sequentially. For example, an oncogene and a polycomb gene may be forcibly expressed, the forced expression may be suppressed, and then an apoptosis suppressor gene may be forcibly expressed, followed by suppressing the forced expression to obtain multinucleated megakaryocytes. Alternatively, an oncogene, a polycomb gene, and an apoptosis suppressor gene can be forcibly expressed simultaneously, followed by suppressing the forced expression simultaneously to obtain multinucleated megakaryocytes. Alternatively, an oncogene and a polycomb gene can be forcibly expressed, and subsequently an apoptosis suppressor gene can be forcibly expressed, followed by suppressing the forced expression simultaneously to obtain multinucleated megakaryocytes. In the present description, the step of forcibly expressing genes may be referred to as the growth phase or proliferation state and the step of suppressing the forced expression may be referred to as the maturation phase.

In the present invention, the "cells more undifferentiated than megakaryocytes" are cells having differentiation potency to megakaryocytes and refers to cells in various differentiation phases from the hematopoietic stem cell system to megakaryocytes. Non-limiting examples of the cells more undifferentiated than megakaryocytes include hematopoietic stem cells, hematopoietic progenitor cells, CD34-positive cells, and megakaryocyte-erythroid progenitor cells (MEP). These cells can be obtained, for example, by isolation from bone marrow, umbilical cord blood, and peripheral blood, and can also be obtained by induced differentiation from pluripotent stem cells such as ES cell and iPS cell, which are far more undifferentiated cells.

In the present invention, the "oncogene" refers to a gene which induces cell neoplastic transformation in vivo and examples include MYC family genes (e.g., c-MYC, N-MYC, and L-MYC), SRC family genes, RAS family genes, RAF family genes, and protein kinase family genes such as c-Kit, PDGFR, and Abl.

The "polycomb gene" is known as a gene for negatively regulating CDKN2a (INK4a/ARF) gene and functions to avoid cellular aging (Ogura et al., Regenerative Medicine, vol. 6, No. 4, pp. 26-32; Jesus et al., Nature Reviews Molecular Cell Biology vol. 7, pp 667-677, 2006; Proc. Natl. Acad. Sci. USA vol. 100, pp 211-216, 2003). Non-limiting examples of the polycomb gene include BMI1, Me118, Ring1a/b, Phc1/2/3, Cbx2/4/6/7/8, Ezh2, Eed, Suz12, HDAC, and Dnmt1/3a/3b.

The "apoptosis suppressor gene" refers to a gene having the function to suppress cell apoptosis and examples include BCL2 gene, BCL-xL gene, Survivin gene, and MCL1 gene.

The forced gene expression and termination of the forced expression can be carried out by the method described in International Publication No. WO2011/034073, International Publication No. WO2012/157586, International Publication No. WO2014/123242, or Nakamura S et al, Cell Stem Cell. 14, 535-548, 2014, other known methods, or methods equivalent thereto. For example, when a drug-responsive gene expression induction system such as Tet-on (Registered trade mark) or Tet-off (Registered trade mark) system is used for the forced gene expression or termination of the forced gene expression, in the step of forced expression, a corresponding drug such as tetracycline or doxycycline may be contained in a medium, and then the drug may be removed from the medium to suppress the forced expression.

Culture conditions for megakaryocytes when carrying out the forced gene expression and suppression (termination) of the forced expression can be typical conditions. For example, the temperature can be about 35° C. to about 42° C., about 36° C. to about 40° C., or about 37° C. to about 39° C., and 5 to 15% $CO_2$ and/or 20% $O_2$ may be employed.

Specifically, the step of forcibly expressing the above genes in the cells more undifferentiated than megakaryocytes can be carried out in accordance with a routine method used by a person skilled in the art and, for example, the step may be achieved when these genes are transfected to cells more undifferentiated than megakaryocytes in the form of a vector which expresses these genes or a protein or RNA encoding these genes. Further, the step can be carried out by allowing a low molecular weight compound or the like which induces the expression of these genes to be in contact with cells more undifferentiated than megakaryocytes.

Vectors expressing these genes include virus vectors such as retrovirus, lentivirus, adenovirus, adeno-associated virus, herpes virus, and Sendai virus, animal cell expression plasmids (e.g., pA1-11, pXT1, pRc/CMV, pRc/RSV, and pcD- NAI/Neo) and the like. Retroviral or lentiviral vector systems are preferred as such an expression can be carried out by a single transfection. Examples of the promoter that can be used in an expression vector include EF-α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR, and HSV-TK (herpes simplex virus thymidine kinase) promoter. In addition to the promoter, the expression vector may contain an enhancer, a poly-A addition signal, a selectable marker gene, an SV40 replication origin and the like. Examples of useful selectable marker gene include dihydrofolate reductase gene, neomycin resistant gene, and puromycin resistant gene.

The gene expression in the expression vector of the present invention may be controlled by tetracycline or doxycycline, for this reason the vector may be a drug-responsive vector having a tetracycline reactive element in the promoter region. In addition, an expression vector in which the loxP sequence is arranged in such a way as to sandwich the gene or promoter region, or both thereof may be used for gene excision from the vector using a Cre-loxP system.

The production of megakaryocytes comprises at least one of (a) a step of treating with an actomyosin complex function inhibitor, and (b) a step of treating with a ROCK inhibitor, while an apoptosis suppressor gene is forcibly expressed in the cultured cells. These treatments can promote more stable proliferation and multinucleation.

Optimum concentrations of an actomyosin complex function inhibitor, a ROCK inhibitor and the like when treating the cells therewith can be determined in advance based on the preliminary experiments by one skilled in the art. Further, the period, method and the like of treatment can also be selected suitably by one skilled in the art. For example, in the case of treatment using blebbistatin, which is a myosin heavy chain II ATPase inhibitor, about 2 to 15 µg/ml or about 5 to 10 µg/ml is added to a culture solution and culture period is, for example, about 5 to 10 days, and particularly preferable about 6 to 7 days. Further, Y27632, which is a ROCK inhibitor, can be used in about 5 to 15 µM or 8 to 12 µM, and preferably about 10 µM. Treatment time with Y27632 is about 10 to 21 days, and preferably about 14 days.

Examples of the ROCK (Rho-associated coiled-coil forming kinase/Rho-binding kinase) inhibitor include [(R)-(+)-trans-N-(4-pyridyl)-4-(1-aminoethyl)-cyclohexanecarboxamide 2HCl·H$_2$O] (Y27632). In some cases, an antibody or a nucleic acid (e.g., shRNA) which inhibits the Rho kinase activity can also be used as the ROCK inhibitor.

After the step of forced expression, the culture step (1) of culturing the megakaryocytes or megakaryocyte progenitor cells obtained in such a step in a platelet producing medium is carried out. In the culture step (1), a method for suppressing or silencing the forced expression may be achieved, for example, when the forced expression is carried out using a drug-responsive vector in the previous step, by not allowing a corresponding drug to be in contact with the cells. Specifically, when the forced gene expression is carried out by doxycycline or tetracycline, the cells are cultured in a medium from which such a drug can be removed to achieve the suppression of forced expression. In addition, when the vector containing LoxP is used, the suppression may also be achieved by transfecting Cre recombinase to such cells. Further, when a transient expression vector and RNA or protein transfection are used, the suppression may also be achieved by stopping the contact with such a vector and the like. The present step can be carried out using the same medium as described above.

The platelet producing medium used in the culture step (1) is not particularly limited and a known medium preferable for producing platelets from megakaryocytes and a medium equivalent thereto can be suitably used. For example, a medium used for culturing animal cells can be prepared as a basal medium. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and mixed medium of these.

The medium may contain serum or plasma, or may be serum free. The medium can also contain one or more substances as needed such as albumin, insulin, transferrin, selenium, fatty acids, trace elements, 2-mercaptoethanol, thiol glycerol, monothioglycerol (MTG), lipids, amino acids (e.g., L-glutamine), ascorbic acid, heparin, non-essential amino acids, vitamins, growth factors, low molecular compounds, antibiotics, antioxidants, pyruvic acid, buffers, inorganic salts, and cytokines. Cytokines are proteins which promote hematopoietic differentiation and examples include vascular endothelial growth factor (VEGF), thrombopoietin (TPO), various TPO-like substances, Stem Cell Factor (SCF), ITS (Insulin-Transferrin-Selenite) supplements, and ADAM inhibitors. A preferable medium in the present invention is IMDM containing serum, insulin, transferrin, selenium, thiol glycerol, ascorbic acid, and TPO. SCF may be added to the medium. Additionally, heparin may be added to the medium. Each concentration is not particularly limited, but for example, TPO can be about 10 ng/mL to about 200 ng/mL, or about 50 ng/mL to about 100 ng/mL, SCF can be about 10 ng/mL to about 200 ng/mL, or about 50 ng/mL, and heparin can be about 10 U/mL to about 100 U/mL, or about 25 U/mL. Phorbol ester (e.g., phorbol-12-myristate-13-acetate; PMA) may also be added.

In the production method according to the present invention, the culture step for megakaryocytes may be carried out under the condition of serum free and/or feeder cell free. The method is preferably carried out by culturing megakaryocytes produced in accordance with the method of the present invention in a medium containing TPO. When the platelet production step is carried out in serum free and feeder cell free conditions, there is less chance for immune reactions when the platelets are used clinically. Further, when platelets can be produced without using feeder cells, the feeder cells do not need to be adhered and thus suspension culture using a flask or the like can be carried out, thereby being suitable for mass production while reducing the production cost. When feeder cells are not used, a conditioned medium may be used. The conditioned medium is not particularly limited and can be produced in accordance with a known method or the like by one skilled in the art but can be obtained by, for example, suitably culturing feeder cells followed by removing the feeder cells from the culture using a filter.

Culture period can be suitably determined while monitoring the number of megakaryocytes and the like but is, for example, 2 days to 10 days, and preferably about 3 days to about 7 days. It is desirable to be at least 3 days or more. Further, it is desirable to suitably carry out passages during the culture period.

A ROCK inhibitor and/or an actomyosin complex function inhibitor is added to the platelet producing medium. Examples of the ROCK inhibitor and actomyosin complex function inhibitor that can be used are the same as those used in the method for producing multinucleated megakaryocytes as described above. Examples of the ROCK inhibitor include Y27632. Examples of the actomyosin complex function inhibitor include blebbistatin, which is a myosin heavy chain II ATPase inhibitor. A ROCK inhibitor may be added singly, a ROCK inhibitor and an actomyosin complex function inhibitor may be added individually, or these may be added in combination.

A ROCK inhibitor and/or an actomyosin complex function inhibitor is preferably added in 0.1 µM to 30 µM and may be added, for example, in 0.5 µM to 25 µM, and 5 µM to 20 µM. The culture period after a ROCK inhibitor and/or an actomyosin complex function inhibitor is added can be 1 day to 15 days, and may be 3 days, 5 days, 7 days or the like.

When a ROCK inhibitor and/or an actomyosin complex function inhibitor is added, a ratio of CD42b-positive platelets can be further increased.

In the present invention, in the culture step of culturing megakaryocytes in the platelet producing medium while suppressing the forced expression, the culture is carried out further in the presence of mechanical stress and platelet production promoting factors including MIF, NRDc, IGFBP2, TSP-1, PAI-1, and CCL5, in addition to the above conditions.

Culture in the presence of mechanical stress refers to that when an external force is applied to a fluid medium, megakaryocytes in the medium are exposed to the mechanical stress such as vortex and shearing strain rate. To expose megakaryocytes to mechanical stress, a medium containing megakaryocytes can be cultured in an incubator capable of generating mechanical stress. Such an incubator is not particularly limited and any incubator may be used as long as it can generate mechanical stress such as vortex and shearing strain rate by stirring using a stirring mechanism provided in a typical flask or inside a large reactor, or by externally applying a predetermined force such as vibration or rotation. Alternatively, a microreactor equipped with pillars used in the Examples can also be used.

The step of exposing megakaryocytes to mechanical stress can also be carried out at the time of starting the step of culturing while suppressing the forced expression, that is, at the time of starting the culture using the platelet producing medium, and can also be carried out 1 to 3 days before the platelet harvest step. Additionally, mechanical stress can be applied intermittently during the culture period but is preferably applied continuously at the time of starting the step of culturing while suppressing the forced expression. In any of the cases, the platelet production promoting factors are preferably promoted to be secreted from megakaryocytes in such a way as to be present in the medium at the time of platelet release from megakaryocytes.

When the above mechanical stress is applied to megakaryocytes in the platelet producing medium, the release of the platelet production promoting factors including MIF, NRDc, IGFBP2, TSP-1, PAI-1, and CCL5 from megakaryocytes is promoted and the amount of MIF, NRDc, IGFBP2, TSP-1, PAI-1, and CCL5 in the medium can be increased. When the amount of these platelet production promoting factors in the medium is increased and the culture is carried out in the presence of these factors while applying the above mechanical stress to the megakaryocytes, the amount of platelets produced per megakaryocyte can be increased. FIG. 1 is a conceptual drawing schematically showing the production of platelets by the method described in the present invention. In reference to the upper drawing, when turbulence by vortex is applied (Vortex Turbulence+) to a medium containing megakaryocytes, the cells release cell product X. When megakaryocytes are cultured in the presence of cell product X and in the presence of the mechanical stress, the release of platelets is promoted, thereby producing functional platelets. In reference to the middle drawing, when megakaryocytes are cultured in the absence of mechanical stress, platelets are not released even when cell product X is present. In reference to the lower drawing, the turbulence is not caused in the medium containing megakaryocytes and when an external force with conditions generating shearing strain is applied, the cells release both cell product X and cell product Y. Cell product Y is an Annexin activator, and platelets released are metabolized at an early stage in vivo and hence platelets unsuitable for blood preparations are produced. More specifically, MIF and IGFBP2 can promote the release of extracellular matrixes from megakaryocytes in the maturation phase. It is considered that extracellular matrixes have an anchoring action among megakaryocytes. Mechanical stress promotes the release of MIF and IGFBP2 from megakaryocytes but MIF and IGFBP2 externally added function in the same manner. On the other hand, $NRD_c$ is released from megakaryocytes by mechanical stress and sheds proplatelets by an endopeptidase activity to produce platelets. This action works in the same manner for NRDc externally added.

Thus, an embodiment in the method of the present invention may comprise at least (b) a step of externally adding platelet production promoting factors including MIF, NRDc, and IGFBP2 to the megakaryocytes. The platelet production promoting factors externally added require three factors- MIF, NRDc, and IGFBP2, but is preferably six factors including TSP-1, PAI-1, and CCL5 in addition to the three factors. This is because six factors enable enhancement of the platelet production from megakaryocytes.

The platelet production promoting factors externally added may be those obtained by any method but are preferably gene recombinants obtained by, for example, genetic engineering techniques. For gene recombinants, commercial products can be used or can be suitably produced by one skilled in the art in accordance with known gene information. For example, MIF, IGFBP2, TSP-1, PAI-1, and CCL5 are commonly available and commercialized proteins can be used. For NRDc, isolation and purification are already reported in J. Biol. Chem., 269, 2056, 1994 and the gene sequence is reported in Proc. Natl. Acad. Sci. USA, 91, 6078, 1994. Thus, NRDc can be produced by a method known in the field concerned based on these literatures or information disclosed in other known literatures. The concentrations of platelet production promoting factors added are not particularly limited and, for example, NRDc, IGFBP2, TSP-1, PAI-1, and CCL5 are added in such a way that the concentration is preferably 10 to 500 ng/mL, and further preferably 50 to 100 ng/mL. MIF is added in such a way that the concentration is preferably 1 to 500 ng/mL, and further preferably 10 to 100 ng/mL. However, these amounts to be added can be suitably determined by a person skilled in the art and are not limited to the above ranges.

The step of externally adding the platelet production promoting factors can be carried out at the time of starting the culture using the platelet producing medium while suppressing forced expression but is preferably carried out 1 to 3 days before the platelet harvest step. This is because the platelet production promoting factors may be deteriorated by the time of platelet harvest step. Further, the factors can be added not only once but several times with time intervals. In any of the cases, the platelet production promoting factors are preferably added in such a way as to be present in the medium at the time of platelet release from megakaryocytes.

In the culture step (1), it is preferably to optionally include a step of controlling the activity of histone deacetylase 6. For the suppression of histone deacetylase 6 activity, HDAC6 inhibitors which inhibit histone deacetylase 6 (HDAC6) can be used and examples of compounds that can be used include
BML-281 (N-Hydroxy-7-[5-(4-tertbutoxycarbonylaminophenyl)-3-isoxazolecarboxamido]heptanamide), Nexturastat A (4-[[Butyl[(phenylamino)carbonyl]amino]methyl]-N-hydroxybenzamide), Tubastatin A hydrochloride (N-Hydroxy-4-[(2-methyl-3,4-dihydro-1H-pyrido[4,3-b]indol-5-yl)methyl]benzamide hydrochloride), Bufexamac (2-(4-Butoxyphenyl)-N-hydroxyacetamide), Droxinostat (4-(4-Chloro-2-methylphenoxy)-N-hydroxybutanamide), Tubacin (N1-[4-[(2R,4R,6S)-4-[[(4,5-diphenyl-2-oxazolyl)thio]methyl]-6-[4-(hydroxymethyl)phenyl]-1,3-dioxan-2-yl]phenyl]-N8-hydroxy-octanediamide), PCI-24781 (3-[(dimethylamino)methyl]-N-[2-[4-[(hydroxyamino)carbonyl]phenoxy]ethyl]-2-benzofurancarboxamide),
1-Naphthonhydroxamic acid (N-Hydroxynaphthalene-1-carboxamide; a-Naphthohydroxamic acid), MC1568 (3-[5-(3-(3-Fluorophenyl)-3-oxopropen-1-yl)-1-methyl-1H-pyrrol-2-yl]-N-hydroxy-2-propenamide), KD5170 (S-[2-[6-[[[4-[3-(Dimethylamino)propoxy]phenyl]sulfonyl]amino]-3-pyridinyl]-2-oxoethyl]ethanethioc acid ester), or Trichostatin A (2,4-Heptadienamide, 7-(4-(dimethylamino)phenyl)-N-hydroxy-4,6-dimethyl-7-oxo-7-(4-(Dimethylamino)phenyl)-N-hydroxy-4,6-dimethyl-7-oxo-2,4-heptadienamide) but not limited thereto.

Further, these HDAC6 inhibitors can control the number of platelets produced in a concentration-dependent manner. BML-281, for example, when added in a concentration of 100 nM or more to a medium, and Nexturastat A, for example, when added in a concentration of 100 nM or more to a medium, can considerably suppress the number of platelets produced. The step of controlling the activity of histone deacetylases is preferably carried out at the time of 0 to 3 days from the start of the culture step.

The enhancement of HDAC6 activity can be carried out by, for example, overexpressing HDAC6 or enhancing relative HDAC6 activity by inhibition of a histone acetyltransferase (HAT).

In the subsequently carried out platelet harvest step, platelets are harvested by a typical method such as FACS from the medium. "Platelet" is one of the cell components in blood and is characterized by CD41a positive and CD42b positive. Platelets play an important role in the thrombus formation and hemostasis along with being involved in tissue regeneration after damages and pathophysiology of inflammation. When platelets are activated by bleeding or the like, receptors of cell adhesion factors such as Integrin αIIBβ3 (glycoprotein IIb/IIIa; complex of CD41a and CD61) are expressed on the membrane thereof. As a result, platelets agglomerate, various blood coagulation factors released from platelets coagulate fibrin thereby to form thrombus and hemostasis proceeds.

The function of platelets can be evaluated based on measurements by known methods. For example, using an antibody against PAC-1 which specifically binds to Integrin αIIBβ3 on the membrane of activated platelets, the amount of the activated platelets can be measured. Alternatively, a platelet activation marker CD62P (P-selectin) is detected using an antibody in the same manner and the amount of the activated platelets can be measured. For example, using flow cytometry, gating is carried out using an antibody against an activation-independent platelet marker CD61 or CD41, followed by detecting bindings of anti-PAC-1 antibody or anti-CD62P antibody. These steps may be carried out in the presence of adenosine diphosphate (ADP).

Further, the evaluation of platelet function can also be carried out by examining whether platelets bind to fibrinogen in the presence of ADP. When platelets bind to fibrinogen, it activates integrin required for the initial phase of thrombus formation.

Figure 6:
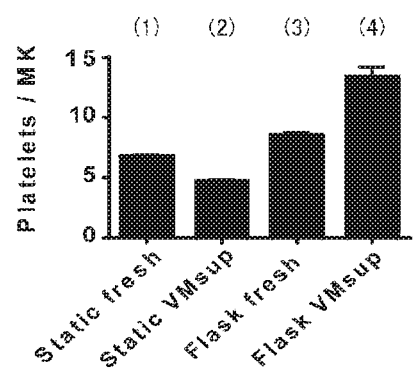
FIG. 6 is a graph showing results of the experiments shown in FIG. 5.

Further, the evaluation of platelet function can also be carried out by a method of observing visualized thrombus formation ability in vivo as shown in FIG. 6 of International Publication No. WO2011/034073.

Platelets obtained by the production method of the present invention can be administered to a patient as a preparation. For administration, platelets obtained by the method of the present invention may be preserved in, for example, human plasma, transfusion, citric acid-containing physiological saline, a solution having glucose acetate Ringer's solution as the main agent, or PAS (platelet additive solution) (Gulliksson, H. et al., Transfusion, 32:435-440, (1992)) and formulated. Preservation period is about 3 days to about 7 days, and preferably 4 days. For preservation conditions, it is desirable to preserve at room temperature (20 to 24° C.) under shaking condition.

In the method for producing platelets by the present method, general culture conditions other than those in the step (a) and the step (b) are cited from US 2012-0238023 A1 (International Publication No. WO2011/034073), US 2014-0127815 A1 (International Publication No. WO2012/157586), and US 2016-0002599 A1 (International Publication No. WO2014/123242), which disclose non-limiting examples of methods for producing megakaryocytes and methods for producing platelets, and are thereby considered as part of the present specification.

[Platelet Production Promoting Agent]

The present invention, according to another embodiment, contains a platelet production promoting agent which contains platelet production promoting factors including MIF, NRDc, and IGFBP2. The platelet production promoting factors further preferably include TSP-1, PAI-1, and CCL5.

When platelet production promoting factors are three components of MIF, NRDc, and IGFBP2, molar ratios thereof may be the same or different. Additionally, when platelet production promoting factors are six components-MIF, NRDc, IGFBP2, TSP-1, PAI-1, and CCL5, molar ratios thereof may be the same or different. These platelet production promoting factors may be those produced by a genetic engineering technique, that is, gene recombinants.

The platelet production promoting agent may be those consisting only of platelet production promoting factors or may contain additives and the like which do not adversely affect these proteins.

The platelet production promoting agent, in the method for producing platelets described earlier, can be used as an additive in the step (b) of externally adding platelet production promoting factors in the culture step.

EXAMPLES

Hereinafter, the present invention is described in more detail in reference to Examples. However, the following Examples do not limit the present invention.

[Preparation of Multinucleated Megakaryocytes]

Cell culture was carried out in accordance with the method described in Cell Culture, Nakamura et al., p. 12 using, as a starting cell, an immortalized megakaryocyte progenitor cell line C1-7 produced by simultaneously transfecting c-MYC, BMI1, and BCL-XL to hematopoietic stem cells derived from iPS cells (TKDN SeV2: iPS cell derived from human fetus skin fibroblasts established using Sendai virus, and 585A1, 585B1, 606A1, 648B1, and 692D2: iPS cells derived from human peripheral blood mononuclear cell established using an episomal vector described in Okita K, et al, Stem Cells 31, 458-66, 2012) established by the method described in Nakamura et al, Cell Stem Cell. 2014 Apr. 3;14(4):535-48 and International Publication No. WO2014/123242. The gene ON medium used for this was an ESC differentiation medium, described in Takayama et al, Blood. 2008 Jun. 1;111(11):5298-306, to which doxycycline 5 μg/ml, and SCF and TPO in concentrations described earlier were added. The cells (also referred to as imMKCL) used in all of the following experiments were prepared by this method.

[1. Comparison in the Numbers of Platelets Produced Between Static Culture and VerMES Shaking Culture]

After turning genes (c-MYC, BMI1, and BCL-XL) off, imMKCL was cultured for 6 days using a platelet producing medium in 10-cm dish static culture (dish), wave bioreactor, and VerMES shaking culture (VerMES). The platelet producing medium (Gene Off medium) used was IMDM with addition of ITS 1x, L-Glu 2 mM, ascorbic acid 50 μg/mL, MTG 450 μM, human plasma 5%, heparin 10 U/ml, human stem cell factor (SCF) 50 ng/ml, TA-316 200 ng/mL, GNF-351 0.5 μM, ROCK (Rho associated protein kinase) inhibitor Y-39983 0.5 μM, and ADAM 17 inhibitor KP457 (Hirata et al., Stem Cell Translational Medicine, in press) 15 μM. Dish means static culture, in which mechanical stress is not generated. VerMES shaking culture can generate mechanical stress throughout the entire culture tank such as homogeneous vorticity, shear stress, and shearing strain rate. Wave bioreactor is an apparatus capable of shaking an incubator in a horizontal direction. CD41a/CD42b-positive platelets and Annexin V positive ratio of platelets were counted by FACS from each of the culture supernatants.

Figure 2:
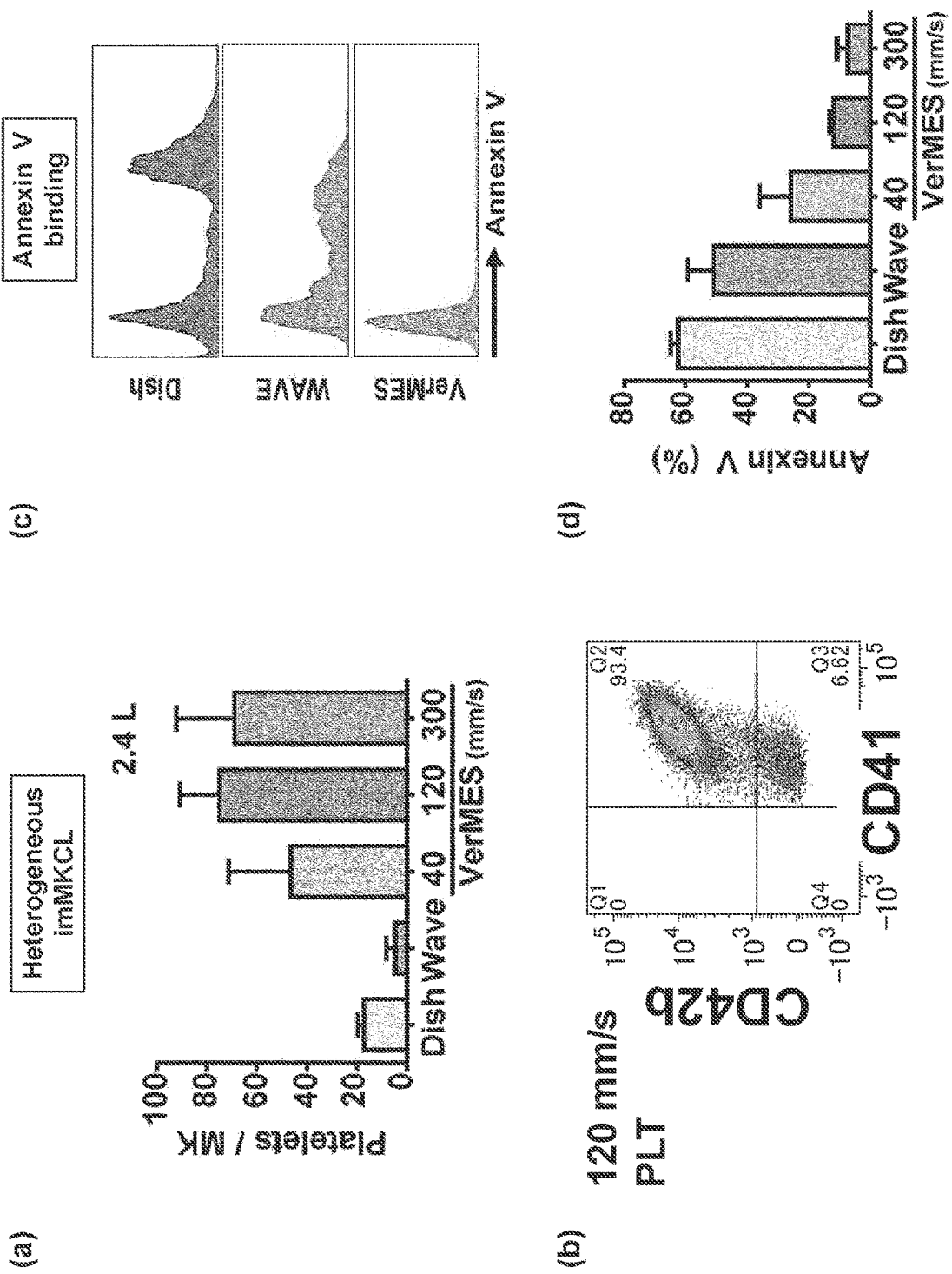
FIG. 2 is a set of drawings for comparisons in the platelet production between static culture and VerMES shaking culture, in which panel (a) is a graph for comparison of the number of platelets produced, panel (b) shows results of CD41$^+$/CD42b$^+$ platelets when counted by FACS, and panels (c) and (d) are graphs for comparisons of Annexin V positive ratio of platelets obtained by static culture, WAVE BAG culture, and VerMES shaking culture.

The results are shown in FIG. 2. In the graph in FIG. 2, panel (a), the vertical axis represents the number of platelets produced per megakaryocyte and the horizontal axis represents each culture condition and stirring speeds of VerMES of 40, 120, and 300 (mm/s). FIG. 2, panel (a) revealed that 60 to 80 platelets were released per megakaryocyte under the optimum culture conditions for VerMES culture. Further, FIG. 2, panel (b) revealed that released platelets were CD41a/42b positive. Annexin V positive ratio must be low for platelets to circulate in vivo. Accordingly, Annexin V positive ratios of released platelets by each of the culture methods were analyzed by FACS. The results are shown in FIG. 2, panels (c) and (d). The platelets released by static culture and wave reactor culture had high Annexin V positive ratios. On the other hand, it was revealed that an Annexin V positive ratio was as low as less than 15% under the optimum culture conditions for VerMES culture.

[2. Comparison in Platelet Function Parameters Between Static Culture and VerMES Shaking Culture]

Figure 3:
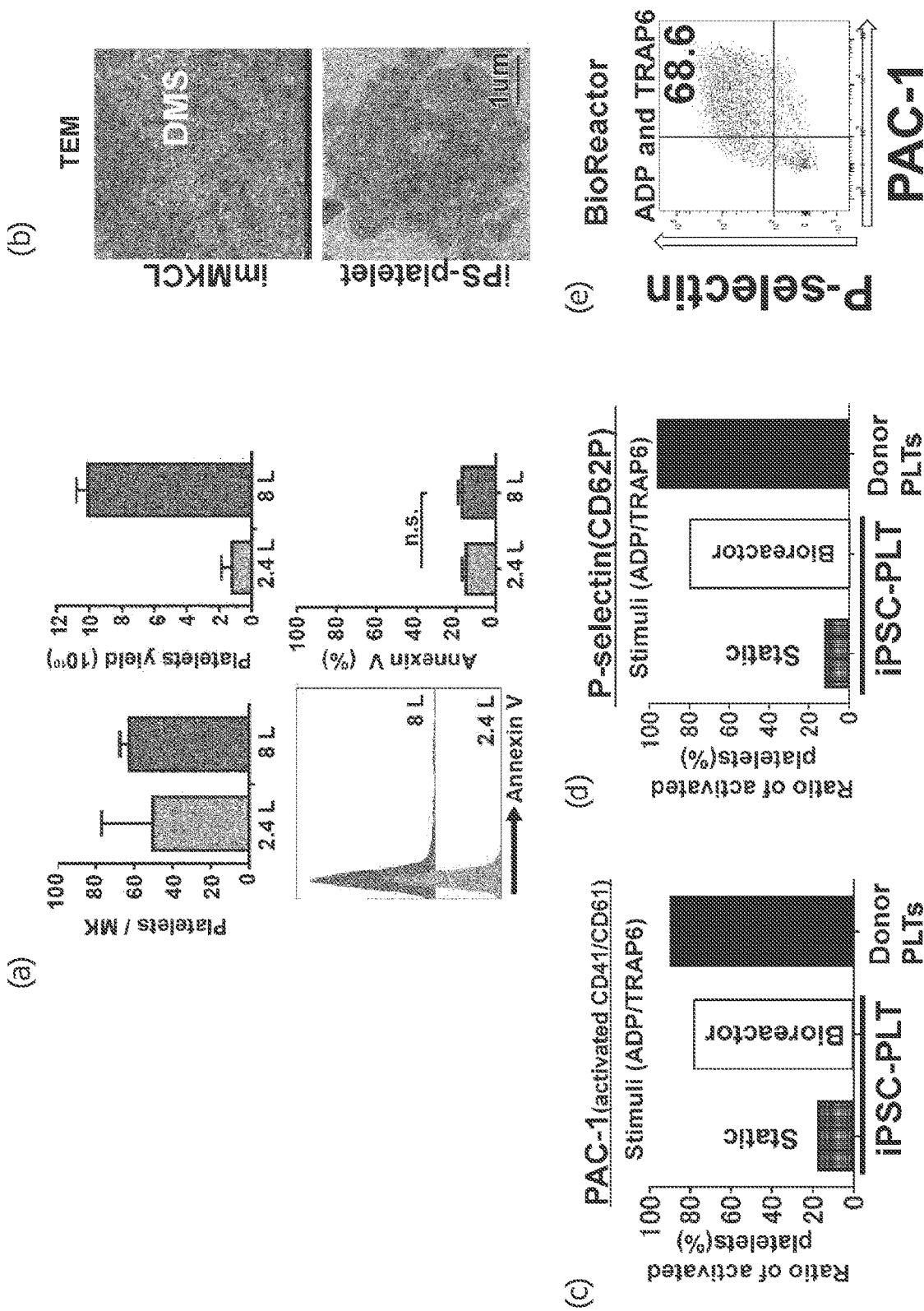
FIG. 3 shows the number of platelets produced and characteristics of the obtained platelets based on the size of incubators and culture methods, in which panel (a) shows that both 2.4 L VerMES and 8 L VerMES had substantially equivalent platelet production and the obtained platelets had a low Annexin V positive ratio in the incubators of both sizes. Upper photograph in panel (b) shows that, in an immortalized megakaryocyte progenitor cell line, the formation of mature DMS is confirmed and a large number of endoplasmic reticula containing many secretory granules are confirmed, and lower photograph shows that mitochondria, a granules, and glycogen granules are observed in platelets produced from an immortalized megakaryocyte progenitor cell line established from iPS cells cultured in a VerMES shaking incubator. In panels (c) and (d), it is shown that VerMES had higher PAC-1 and P-selectin (CD62P), respectively, when compared with static culture, and is comparable to the donor-derived platelets. These are platelet function parameters and is measured by FACS. A FACS image of PAC-1 and P-selectin (CD62P) of platelets obtained by VerMES shaking culture is shown in panel (e).

After turning genes (c-MYC, BMI1, and BCL-XL) off, megakaryocytes were cultured for 6 days in the same manner as above using a platelet producing medium by 2.4L and 8L VerMES shaking cultures (VerMES). Cultured megakaryocytes and platelets were observed using an electron microscope (TEM). CD41a/CD42b-positive platelets and Annexin positive ratios of platelets were counted by FACS from the culture supernatants after the cultures. Additionally, PAC1/P-selectin positive ratio of platelets was counted by FACS to analyze functions of platelets. The results are shown in FIG. 3. Platelet production in 8 L VerMES was substantially equivalent to that produced in 2.4 L VerMES and succeeded in obtaining about $1 \times 10^{11}$ platelets. The obtained platelets were healthy platelets with a low Annexin V positive ratio in both the incubators used.

The megakaryocyte cell line cultured in VerMES and the produced platelets were observed using an electron microscope. Upper panel in FIG. 3, panel (b) confirmed the formation of mature DMS in the immortalized megakaryocyte cell line and a large number of endoplasmic reticula containing many secretory granules. Mitochondria, a granules, and glycogen granules were observed in the platelets produced in a VerMES shaking incubator from the immortalized megakaryocyte cell line established from iPS cells shown in lower panel in FIG. 3, panel (b) thereby confirming the structure to be substantially equivalent to that of peripheral blood platelets. The platelets produced in a culture dish by static culture, the platelets produced by 2.4 L scale culture using a VerMES shaking incubator, and the peripheral blood platelets were measured by FACS for PAC-1 and P-selectin, which are platelet function parameters in vitro. The results are shown in FIG. 3, panels (c) to (e). It was revealed that these platelets had function activities substantially equivalent to those of peripheral blood platelets, and that these platelets had function activities apparently different from those of platelets obtained by static culture.

[3. Comparison in mRNA Between Static Culture and VerMES Shaking Culture]

Figure 4:
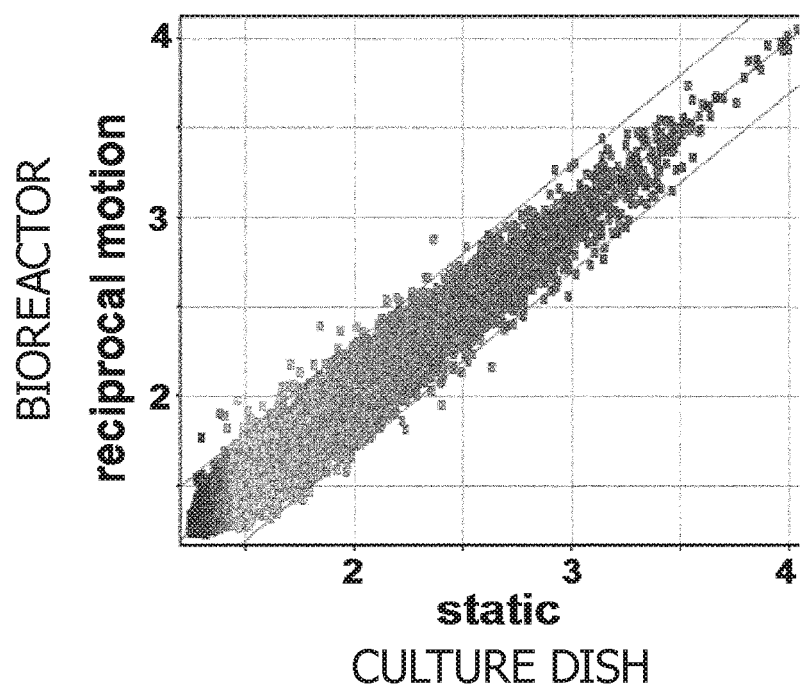
FIG. 4 shows that when RNA of imMKCL cultured by static culture and VerMES shaking culture were harvested and analyzed by microarray, the results found no differences in mRNA.

After turning genes (c-MYC, BMI1, and BCL-XL) off, RNA was harvested from imMKCL cultured for 3 days using a platelet producing medium in 10-cm dish static culture and VerMES shaking culture, and analyzed by microarray. The results are shown in FIG. 4. Both culture conditions showed substantially equivalent gene expression patterns and no difference was found in mRNA.

[4. Comparison in the Numbers of Platelets Produced by Culture Methods and Culture Conditions]

Figure 5:
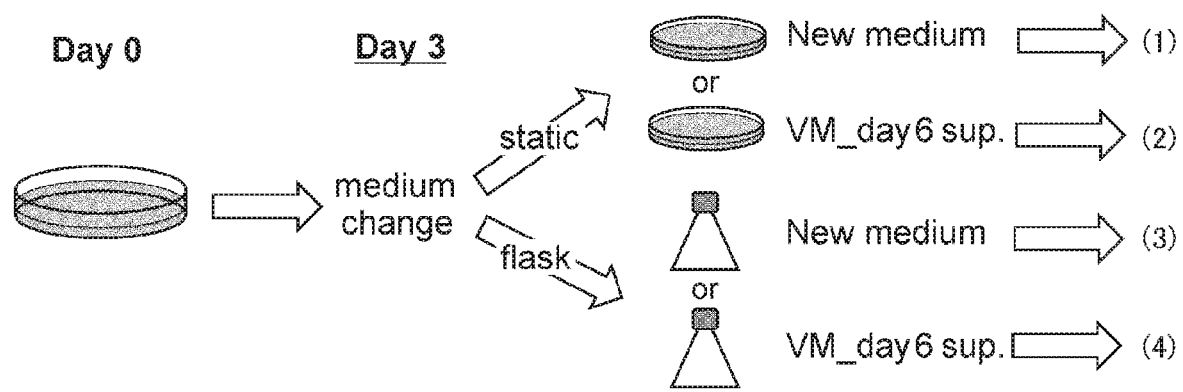
FIG. 5 is a conceptual drawing showing an overview of experiments conducted to compare the number of platelets produced by different culture methods and culture conditions.

After turning genes (c-MYC, BMI1, and BCL-XL) off, imMKCL was subjected to static culture in a 10 cm dish for 3 days using a platelet producing medium. Subsequently, the culture was carried out for 3 days under 4 conditions: (1) a group in which the medium was replaced with a new platelet producing medium, (2) a group in which the medium was replaced with the Day 6 medium of VerMES shaking culture (VM_day 6sup.), (3) a group in which the medium was replaced with a new platelet producing medium and flask culture was carried out, and (4) a group in which the medium was replaced with the Day 6 medium of VerMES shaking culture and flask culture was carried out. Herein, the static culture means no turbulence stress, and the flask culture means that turbulence stress was generated by shaking flask. Additionally, the Day 6 medium of VerMES shaking culture refers to a megakaryocytes- and platelets-free supernatant obtained by subjecting imMKCL to shaking culture after turning genes (c-MYC, BMI1, and BCL-XL) off using a platelet producing medium and VerMES for 6 days in the same manner as in the present experiment and subsequently centrifuging the culture supernatant, followed by filtration using a filter. CD41a/CD42b-positive platelets were counted by FACS. FIG. 5 shows an overview of the present test and FIG. 6 shows the results. In the graph of FIG. 6, the Y axis is the number of platelets produced per megakaryocyte and the X-axis is each culture condition. From the result, no considerable differences in the platelet production under the static condition could be observed. On the other hand, in the flask cultures the number of platelets produced increased in the group in which the medium was replaced with the VerMES culture supernatant when compared with the group in which the medium was replaced with a new medium.

Note that a slight rise in the number of platelets produced is recognized even in the new medium due to the shaking flask culture (shear++/a condition in which little turbulence was probably generated). These results revealed that platelet production promoting factors are contained in the VerMES culture supernatant and platelet production promoting factors and mechanical stress of turbulence are needed for the improvement in production efficiency.

[5. Comparison in Culture Supernatant Protein Arrays Between Static Culture and VerMES Shaking Culture]

Figure 7:
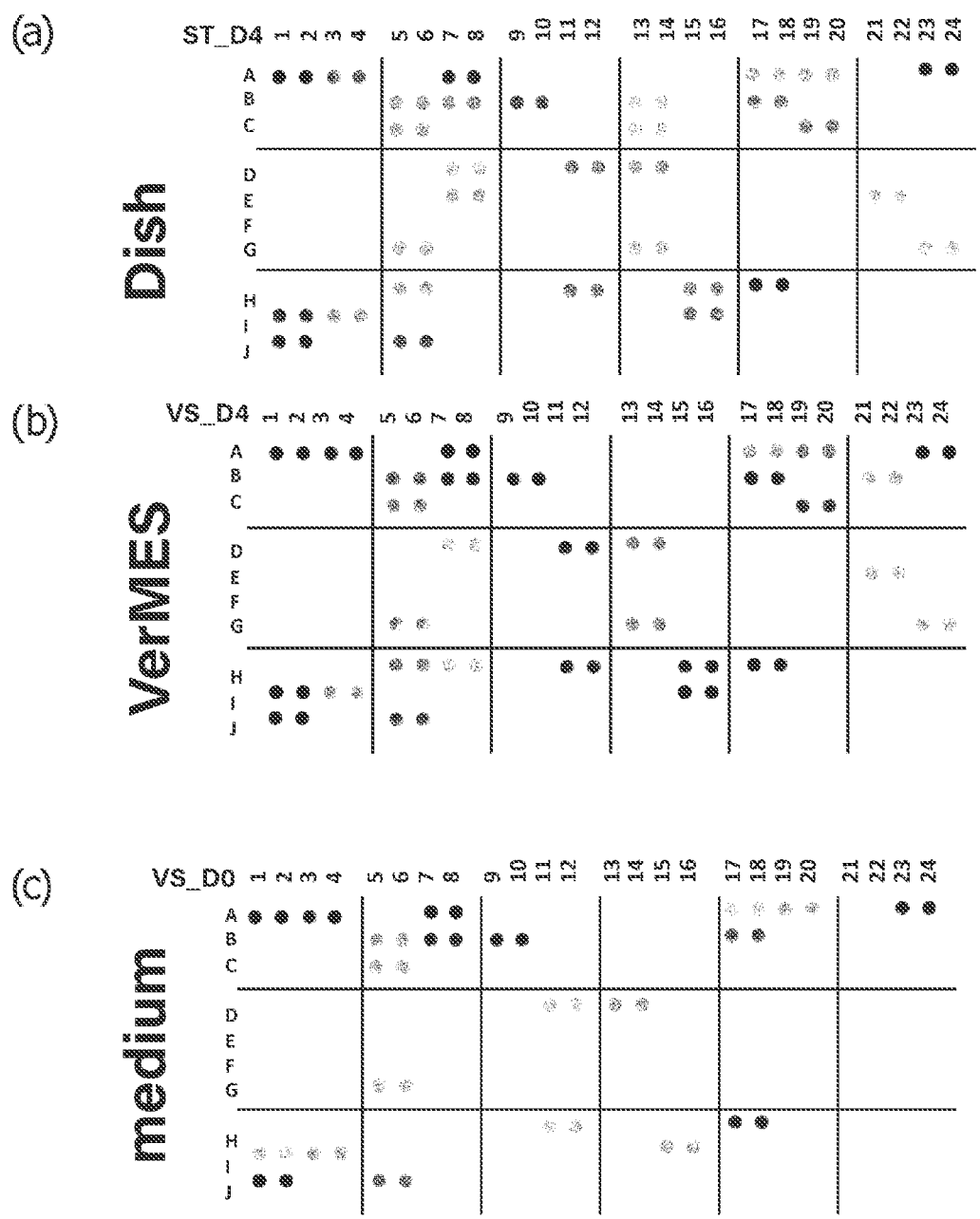
FIG. 7, panels (a), (b) and (c) is a set of photographs showing appearances of the arrays after protein arrays analysis.

Each of the culture supernatants obtained by, after turning genes (c-MYC, BMI1, and BCL-XL) off, culturing imMKCL for 6 days using a platelet producing medium in 10-cm dish static culture (Dish) and VerMES shaking culture (VerMES) and a platelet producing medium (medium) which was not allowed to contact megakaryocytes for the control were harvested to carry out protein array using Proteome profiler Cytokine Array Kit (ARY006, R&D Systems, Inc.). Chemiluminescence signals were detected using ELISA assay system. Details are as described in Tamura and Suzuki-Inoue et al., Blood, 2016; 127(13):1701-10 and Yumimoto K et al., J Clin Invest, 2015;125(2):621-635.FIG. 7 is a set of photographs showing appearances of the arrays after reaction.

Figure 8:
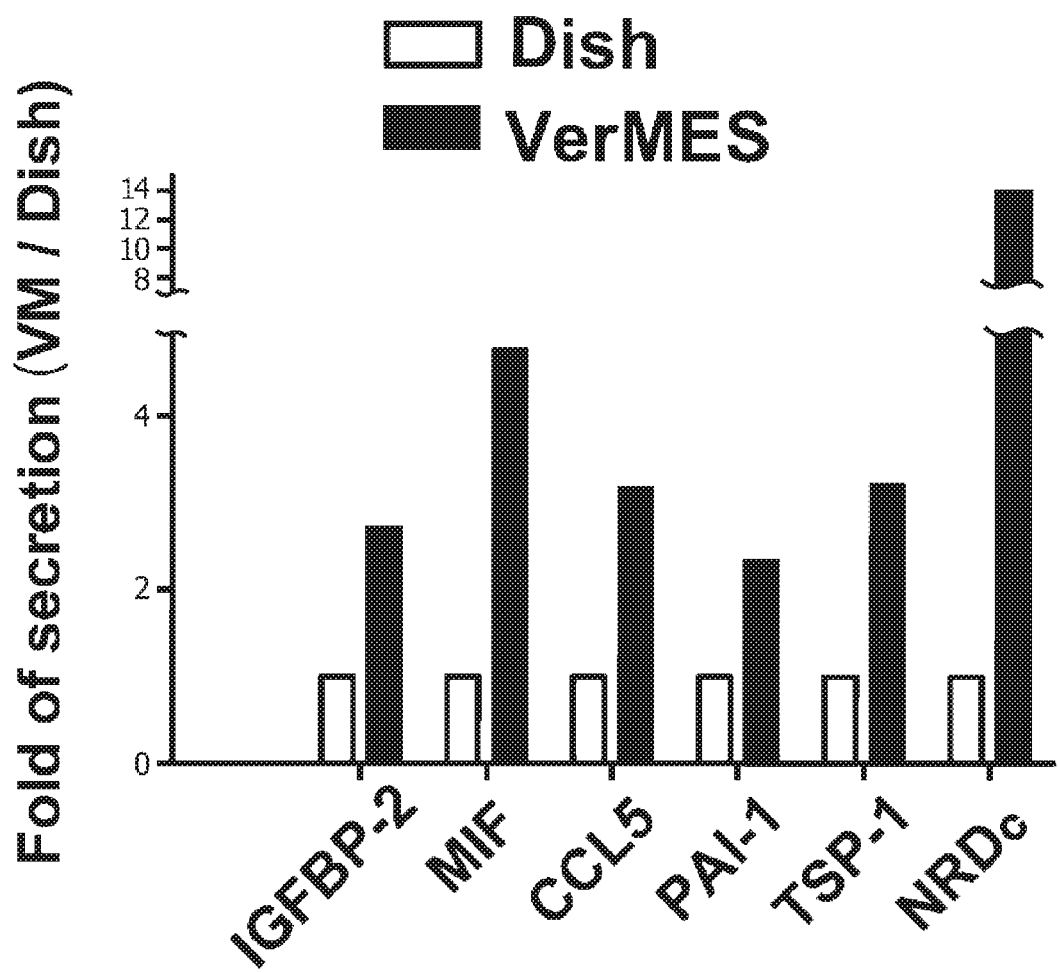
FIG. 8 is a graph showing protein array analysis results. The vertical axis represents the signal from each protein (IGFBP2, MIF, CCLS, PAI-1, TSP-1, and NRDc) when compared to the relative signal from static culture assumed as 1. The horizontal axis represents each factor.

FIG. 8 shows the protein array analysis results. The Y axis corresponds to the relative value of signals from proteins IGFBP2, MIF, CCL5, PAI-1, TSP-1, and NRDc in VerMES culture supernatant when compared to the signal from static culture supernatant which is considered as 1 and the X-axis corresponds to each factor. The results revealed that the VerMES culture supernatant contains a large number of six factors, IGFBP2, MIF, CCL5, PAI-1, TSP-1, and NRDc when compared with the static culture supernatant. On the other hand, it was observed that the static culture supernatant contains a large number of IL-8, which is not shown in the figure, when compared with the VerMES culture supernatant.

[6. Behavior Observation of Proteins by Immunostaining]

Figure 9:
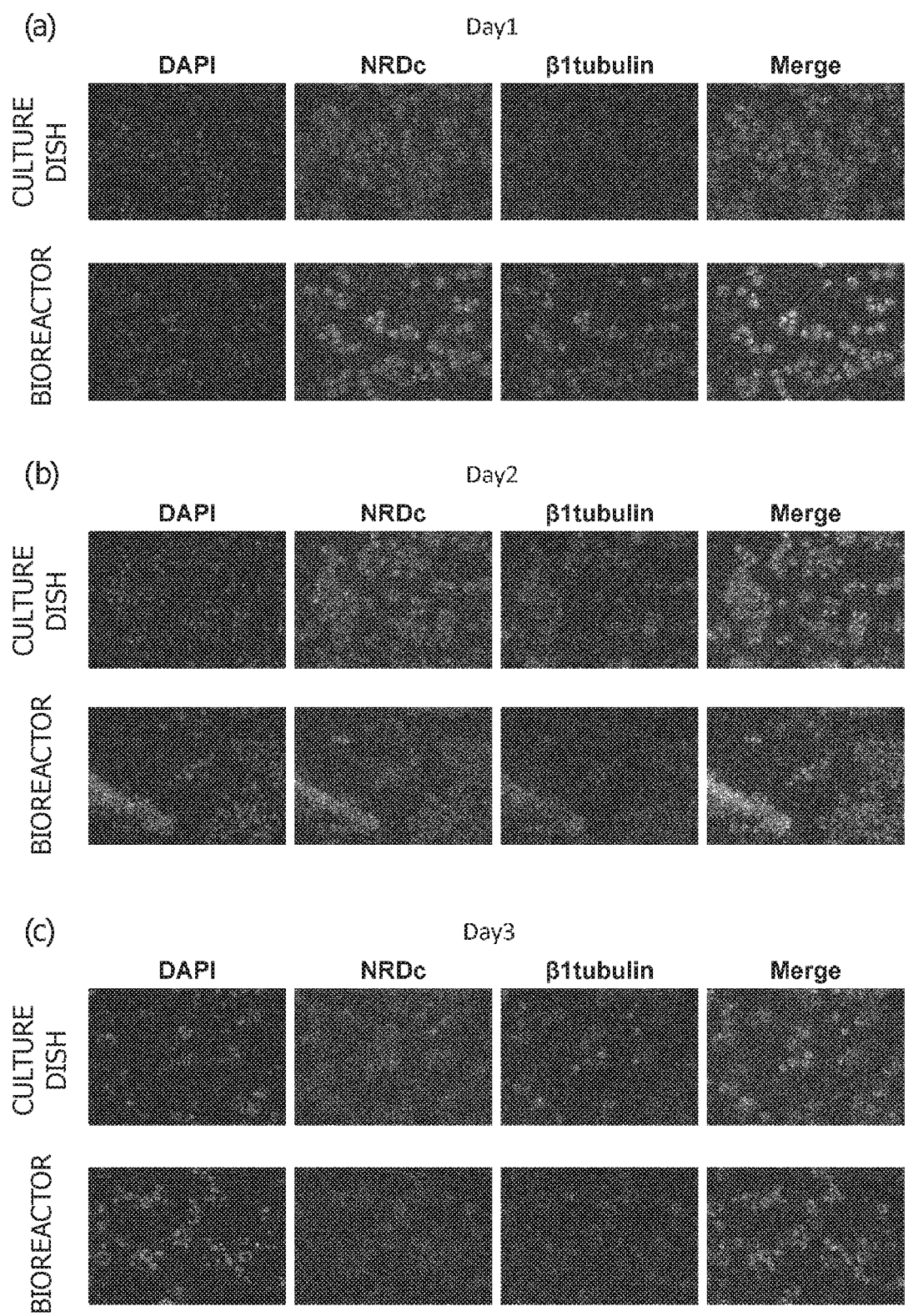
FIG. 9, panel (a) is a set of photographs showing that a large number of NRDc and β-tubulins are present in the nuclei in both static culture and VerMES culture on Day 1 of platelet production induction, panel (b) is a set of photographs showing that NRDc and β1-tubulin are partially present in the cytoplasm but most of them are present in the nuclei in both static culture and VerMES culture on Day 2, and panel (c) is a set of photographs showing that most of NRDc and β1-tubulin are present in the cytoplasm in both static culture and VerMES culture on Day 3.
Figure 10:
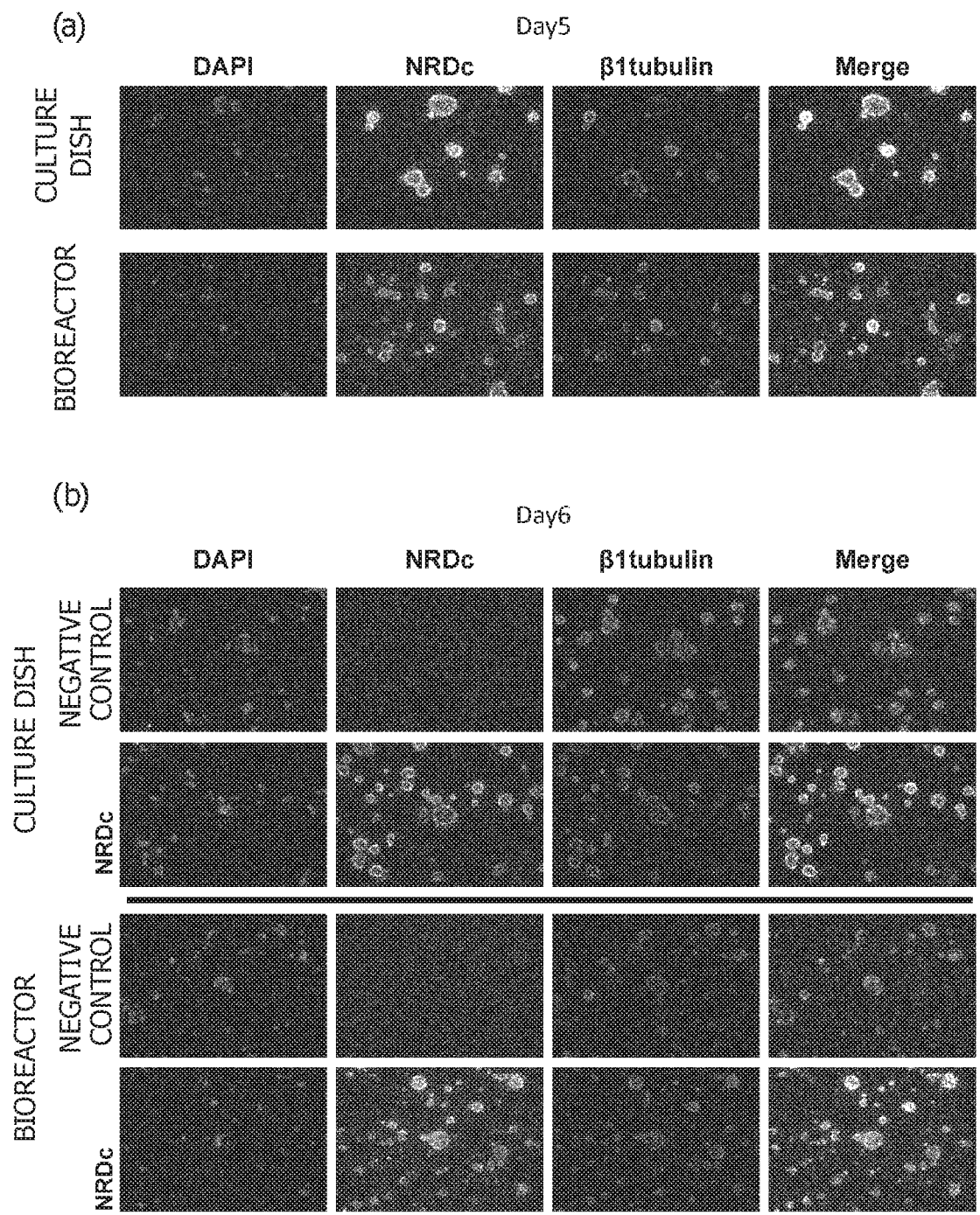
FIG. 10, panel (a) is a set of photographs showing that most of NRDc and β1-tubulin are present on the cell membrane in both static culture and VerMES culture on Day 5 of platelet production induction, and panel (b) is a set of photographs showing that most of NRDc and β1-tubulin are present on the cell membrane in both static culture and VerMES culture on Day 6.

Subsequently, proteins conforming with the behavior of beta 1-tubulin, which is a megakaryocyte mature molecule, were searched for. An imMKCL culture, after turning genes (c-MYC, BMI1, and BCL-XL) off, and culturing for 1 to 6 days using a platelet producing medium in 10-cm dish static culture (dish) and VerMES shaking culture (VerMES), platelets were harvested. From Day 1 to Day 6, the cells of each day were fixed on glass slides, immunostained with DAP1, NRDc, and β1-tubulin, and then observed using a fluorescence microscope. The results are shown in FIG. 9 and FIG. 10. In reference to FIG. 9, panel (a), a large number of NRDc and β1-tubulin are present in the nuclei in both static culture and VerMES culture on Day 1 of the platelet production induction. In reference to FIG. 9, panel (b), NRDc and β1-tubulin are partially present in the cytoplasm but most of them are present in the nuclei in both static culture and VerMES culture on Day 2 of the platelet production induction. In reference to FIG. 9, panel (c), most of NRDc and β1-tubulin are present in the cytoplasm in both static culture and VerMES culture on Day 3 of the platelet production induction. In reference to FIG. 10, panel (a), most of NRDc and β1-tubulin are preset in the cell membrane in both static culture and VerMES culture on Day 5 of the platelet production induction. In reference to FIG. 10, panel (b), most of NRDc and β1-tubulin are present in the cell membrane in both static culture and VerMES culture on Day 6 of the platelet production induction. The above results revealed that the behavior of NRDc and β1-tubulin conform with each other, and NRDc and β1-tubulin are present in the nuclei on Days 1 to 2 of the platelet induction and migrate to the cell membrane day by day. DAPI is a nuclear labeling marker which binds to DNA and exhibits fluorescence.

[7. Behavior Confirmation of Proteins by Western Blot]

Figure 11:
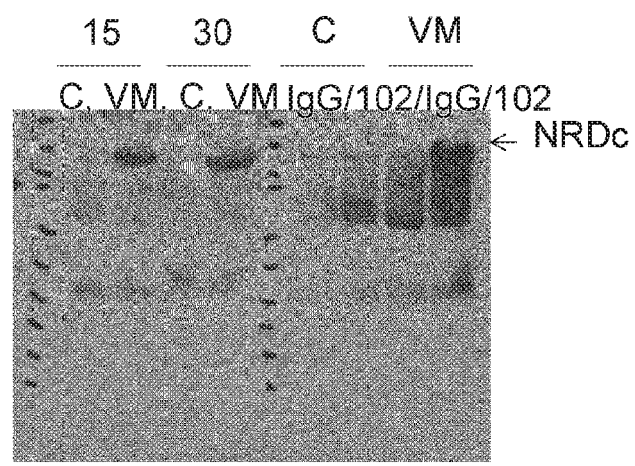
FIG. 11 shows results of the western blot using an anti-NRDc antibody when each culture supernatant of imMKCL cultured in dish static culture (Dish) or VerMES shaking culture (VerMES) was concentrated.

Subsequently, molecules which are highly expressed in megakaryocytes and have the same protein behavior as β1-tubulin, which is a mature molecule, were searched for. Each of the culture supernatants obtained by, after turning genes (c-MYC, BMI1, and BCL-XL) off, culturing imMKCL for 6 days using a platelet producing medium in 10-cm dish static culture (Dish) and VerMES shaking culture (VerMES) with stirring at a speed of 120 mm/s was concentrated with AMICON ULTRA (Merck Millipore) and subjected to western blot using an anti-NRDc antibody. The results are shown in FIG. 11. In the figure, 15 and 30 are the centrifugation times (min) at the time of concentration. In the case of 15 minutes, an amount of concentration was 80 μm and 6-fold concentration, whereas in the case of 30 minutes, an amount of concentration was 48 μm and 10-fold concentration. The detection method was as follows. Additionally, C refers to static supernatant and V refers to VerMES shaking culture supernatant.

Concentration (left lane); 15 minutes, 30 minutes

IP (right lane); #102 3 μg, sup 200 μl, ProG 20 μl+PIC

FIG. 11 shows the result of each blotted sample with the anti-NRDc antibody. The NRDc secretion increased in VM even when the supernatant was concentrated or IP was carried out using the anti-NRDc antibody thereby revealing that a large number of NRD-1 was contained in the VerMES culture supernatant.

Figure 12:
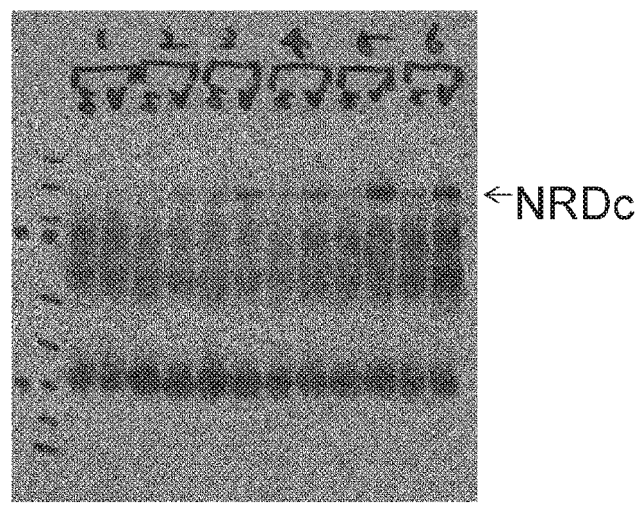
FIG. 12 shows results of the western blot using an anti-NRDc antibody when imMKCL was cultured for 1 to 6 days in dish static culture (Dish) or VerMES shaking culture (VerMES) and culture supernatants of each day platelet production induction from Day 1 to Day 6 were concentrated.

After turning genes (c-MYC, BMI1, and BCL-XL) off, imMKCL was cultured for 1 to 6 days using a platelet producing medium in 10-cm dish static culture (Dish) and VerMES shaking culture (VerMES) with stirring at a stirring speed of 120 mm/s, concentrated with AMICON ULTRA (Merck Millipore), and subjected to western blot using an anti-NRDc antibody. From Day 1 to Day 6, the culture supernatants of the platelet production induction of each day were subjected to western blot. The supernatant was centrifuged for 15 minutes and 500 μl of the sample was concentrated with a concentration factor of 6 and 12 μl of this concentrate was used for electrophoresis. FIG. 12 shows the result of each blotted sample with the anti-NRDc antibody. It was revealed that a large number of NRDc was contained in the VerMES culture solution on Day 5 of the platelet production induction. The above results revealed that a large number of NRDc was secreted from the megakaryocyte cell line by the VerMES culture.

[8. Experiment Using Fluid Bioreactor Chip]

Figure 13:
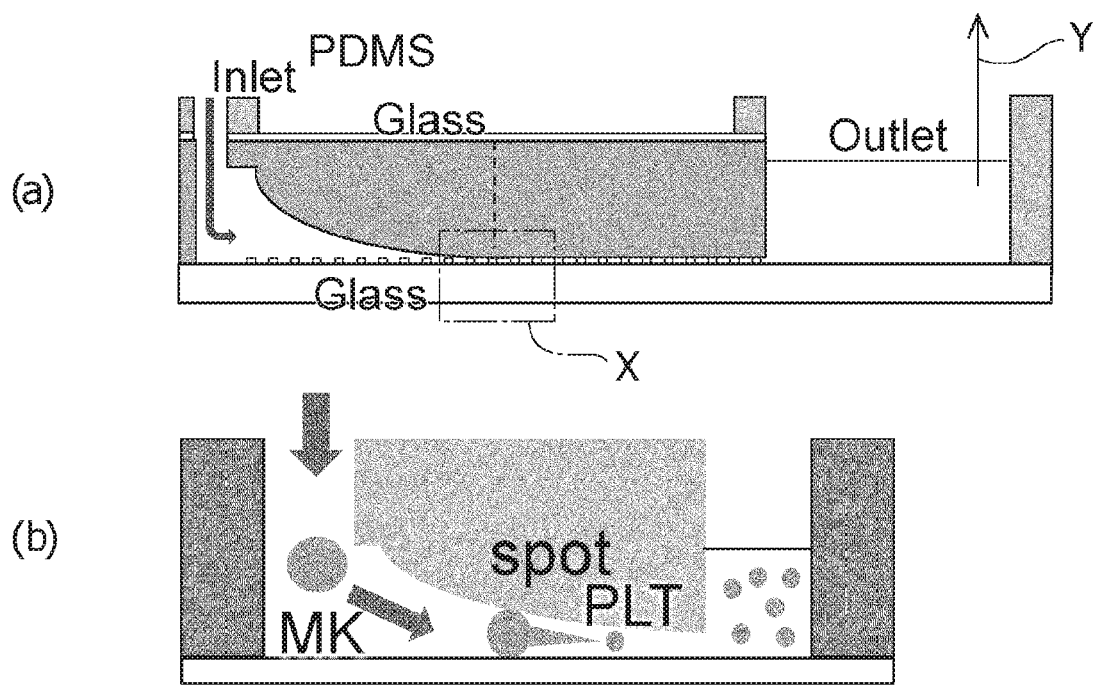
FIG. 13, panel (a) is a drawing showing the cross sections of fluid bioreactor chip used in Examples, and panel (b) schematically shows the behavior of megakaryocytes at the time of introducing a medium containing megakaryocytes to the bioreactor chip.
Figure 14:
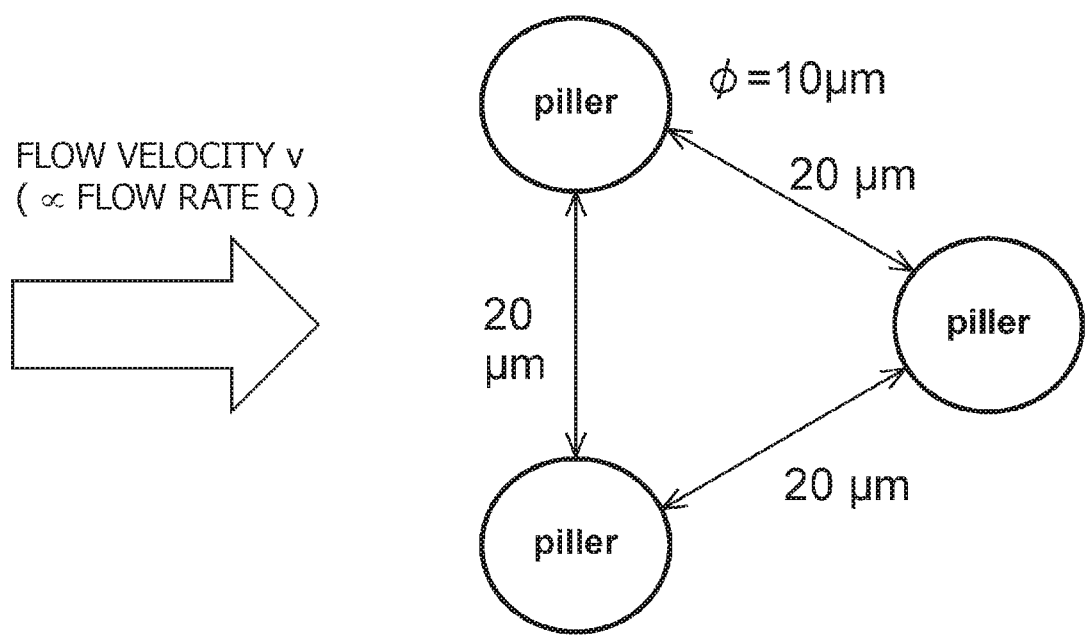
FIG. 14 schematically shows the direction of flow velocity and the arrangement of pillars, and the relative positional relation among the pillars, in the fluid bioreactor chip shown in FIG. 13.
Figure 15:
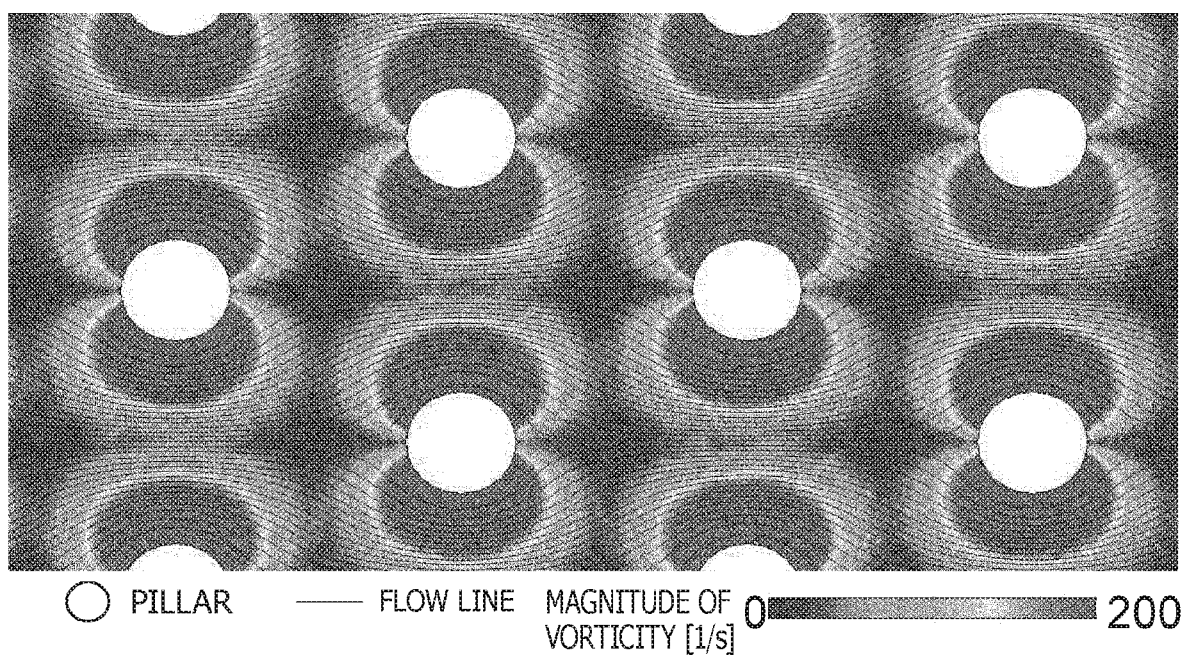
FIG. 15 is a drawing showing the simulation result of vorticity around the pillars of the fluid bioreactor chip shown in FIG. 13, and shows that a vorticity of about 200 s$^{-1}$ is generated around the pillars.

An experiment was carried out to investigate whether the six candidate proteins, TSP-1, PAI-1, CCL5, NRDc, MIF, and IGFBP2 are involved in the promotion of platelet production. In this experiment, the number of platelets produced under each culture condition was counted using a fluid bioreactor chip which generates a vortex. The fluid bioreactor chip used was an apparatus developed by and received from Fumihito Arai, et al., Nagoya University. FIG. 13 shows the apparatus used. FIG. 13, panel (a) is a drawing showing the cross section of the apparatus. The medium containing megakaryocytes, which is the sample, is injected from an entrance indicated as Inlet in the direction of an arrow. A number of pillars having a diameter of 10 μm are present at the bottom of the apparatus. These pillars are present not only in the direction of flow channel as confirmed in FIG. 13, panel (a) but also in the transverse direction. The pillars are arranged in such a way as to have a positional relation in which each pillar center forms an equilateral triangle having a side of 30 μm and the flow direction is perpendicular to a side of the equilateral triangle (FIG. 14). In the apparatus, the height of flow channel gradually decreases along with the flow of a sample and, stays at a constant height at the position shown with a dotted line in FIG. 13, panel (a). Further, a fluorescence microscope photograph can be taken at the position X using a microscope, which is not shown in the drawing. A position Y at which the height of flow channel becomes wider again is Outlet, from which a sample can be harvested. The arrangement of pillars shown in FIG. 14 generates vortexes in the apparatus, and simulation revealed that a vorticity of about 200 s$^{-1}$ is generated around the pillars (FIG. 15). In reference to FIG. 13 again, FIG. 13, panel (b) schematically shows the behavior of megakaryocytes at the time of introducing a medium containing megakaryocytes to such an apparatus. A megakaryocyte shown as MK is exposed to shear stress, shearing strain rate, and vortexes generated by the pillars, and platelet shedding is mainly caused in the vicinity of the site where the height of flow channel becomes narrow, and in the vicinity of the Outlet where the medium in which platelets are produced is expected to flow out.

After fixing the bioreactor chip under a fluorescence microscope, imMKCL cultured for 5 days using a platelet producing medium in 10-cm dish static culture (dish) was introduced to the inlet of the chip. After delivering the platelet producing medium incubated at 37° C. of each condition, time-lapse observation was carried out for 4 hours using a fluorescence microscope on the frame shown as X in FIG. 13, panel (a). Four hours after delivery, platelets were harvested from each medium and CD41a/CD42b-positive platelets were counted by FACS. Medium conditions included a control medium (the same medium as used in the earlier experiment 5), a six factors-containing medium (control medium+six factors: 6F), and mediums in which 1 factor each was removed from the six factors (6F−1 protein), specifically, a medium in which thrombospondin 1 was removed from six factors (6 factors −TSP1), a medium in which PAI-1 was removed from six factors (6 factors −PAI-1), a medium in which CCL5 was removed from six factors (6 factors—CCL5), a medium in which NRDc was removed from six factors (6 factors −NRDc), a medium in which MIF was removed from six factors (6 factors −MIF), and a medium in which IGFBP2 was removed from six factors (6 factors −IGFBP2). Note that six factors are candidate proteins TSP-1, PAI-1, CCL5, NRDc, MIF, and IGFBP2 confirmed in the earlier experiments, and a concentration of each protein in the six factors-containing media was 10 ng/ml for MIF and 50 ng/ml for other 5 factors. Further, a medium containing a dominant-negative structure of NRDc (Hiraoka et al., Biochem Biophys Res Commun. 2008 May 23; 370(1):154-8) in place of NRDc of the six candidate proteins and other five candidate proteins was used (5F+NRDc_DN). The dominant-negative structure of NRDc has a zinc binding motif deleted and the endopeptidase activity deactivated. Also, in the medium containing the dominant-negative structure, a concentration of each protein was 10 ng/ml for MIF and 50 ng/ml for other 5 factors.

Figure 16:
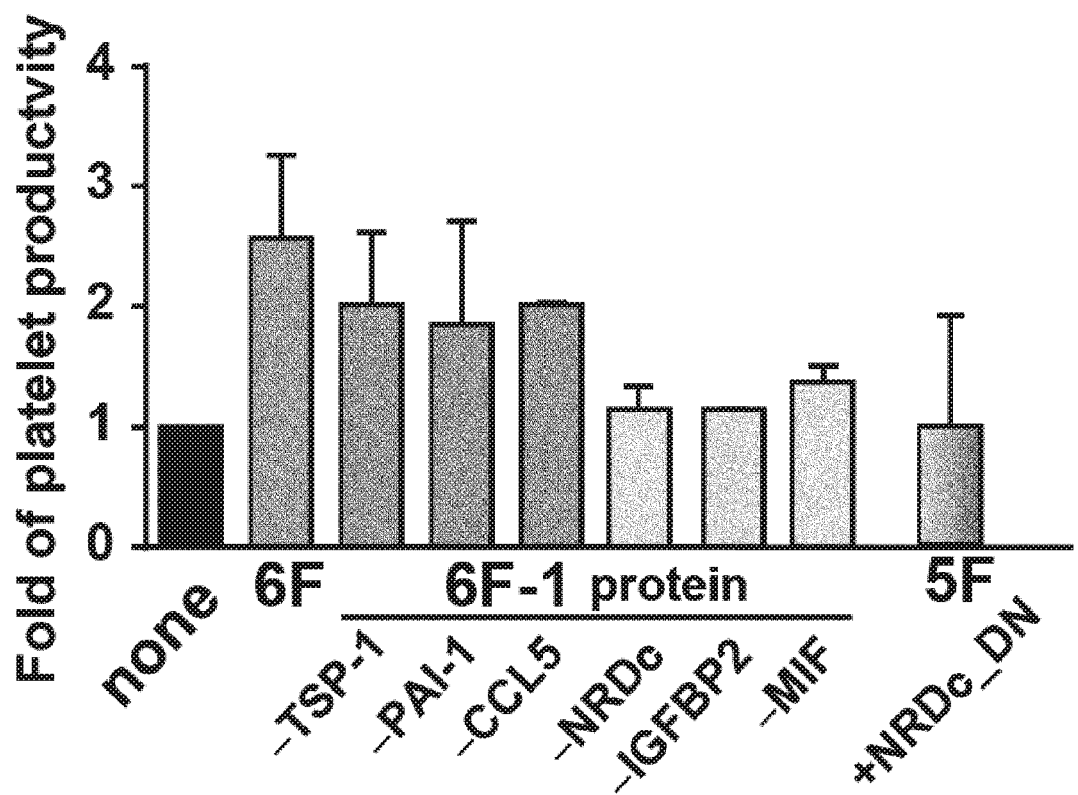
FIG. 16 shows that the number of platelets produced significantly increases in the medium containing six candidate proteins when compared with the control medium. The number of platelets produced reduces when each of the candidate proteins are removed from the culture medium when compared to the platelet production in the six candidate proteins-containing medium. Among the six candidate proteins, instead of NRDC, the number of platelets produced in the medium containing NRDc dominant negative structure and the other five candidate proteins is similar to that in in the control medium, and is considered that the endopeptidase activity of NRDc is essential for at least platelet production.

FIG. 16 shows the count results of CD41a/CD42b-positive platelets. In the graph, the Y axis shows the number of platelets produced per megakaryocyte when compared to the relative production in the control medium assumed as 1, and the X-axis represents each culture condition. The graph revealed that the numbers of platelets produced significantly increased in the six candidate proteins-containing medium when compared with the control medium. On the other hand, it was revealed that the number of platelets produced decreased under the medium conditions in which each of the candidate proteins was removed when compared with the six candidate proteins-containing medium, and the number of platelets produced significantly decreased particularly in the media from which MIF, NRDc, and IGFBP2 were removed. Further, the number of platelets produced in the medium containing the dominant-negative structure and other 5 candidate proteins was about the same as that in the control medium. These findings proved that the endopeptidase activity of NRDc sheds proplatelets at least for the platelet production in this system.

Additionally, FIG. 17 shows a set of representative photographs obtained using a fluorescence microscope and showing the platelet production in the chip. In each photograph, green indicates the megakaryocyte cell line. FIG. 17, panel (a) is a representative photograph showing each medium of six factors medium, 6 factors—thrombospondin, and 6 factors—PAI-1. A large number of ProPlatelet Formation (PPF) is confirmed. Since the number of platelets produced is large, it is assumed that the platelets were sheared off from PPF. FIG. 17, panel (b) is a representative photograph showing 6 factors—NRDc. PPF equivalent to that in FIG. 17, panel (a) was confirmed but the number of platelets produced was small, which indicated that the PPF shearing was not efficient. FIG. 17, panel (c) is a representative photograph showing each medium of control medium, 6 factors—MIF, and 6 factors—IGFBP2. It was revealed that megakaryocytes, without binding or adhering to a glass surface, do not attach as desired and thus all of the megakaryocytes are swept away by the flow velocity of culture solution thereby failing to form a platelet production site, whereby PPF itself was not achieved.

[9. Effects of Recombinant Addition]

Figure 18:
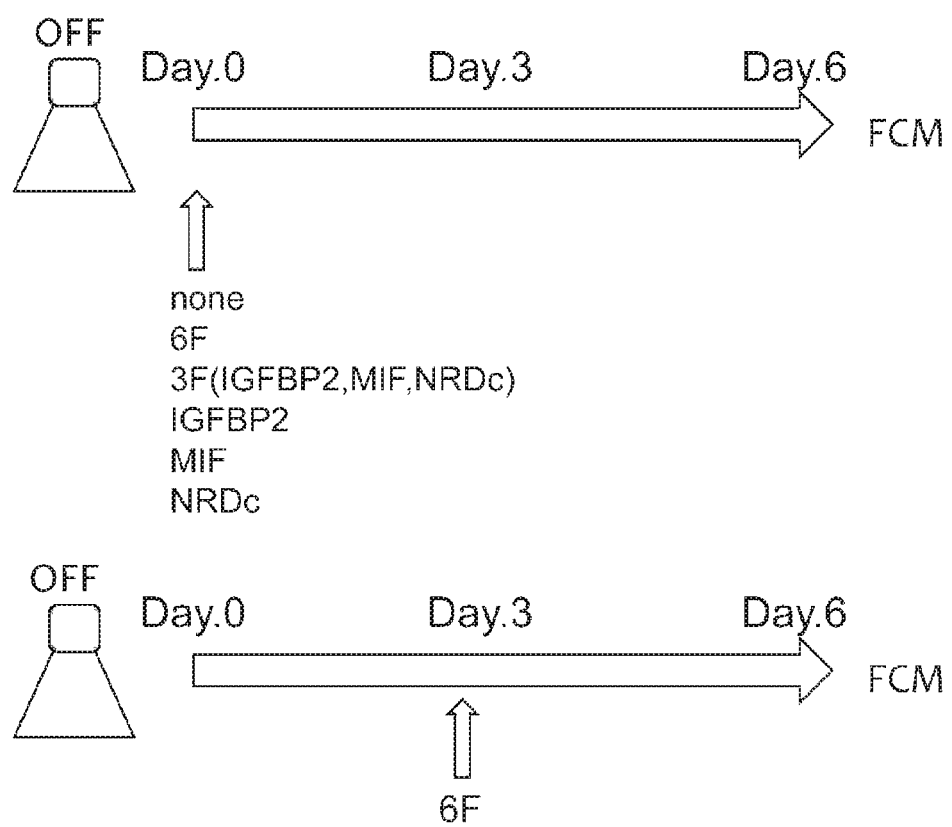
FIG. 18 is a drawing showing an overview of the experiments for comparing the platelet production effects by addition of six recombinant factors.

After turning genes (c-MYC, BMI1, and BCL-XL) off, imMKCL was subjected to shaking flask culture using a platelet producing medium in the same manner as above. For culture conditions, 25 ml of the cells in 1×10$^5$ cells/ml concentration were seeded in an E125 flask and cultured with shaking at 37° C., 5% CO$_2$, and a revolution of 100 rpm. For the basic composition (none) of the platelet producing medium, GNF351 0.5 μM, Y39983 0.5 μM, and KP457 10 μM were added to IMDM (5% HP). Additionally, a medium in which six factors of recombinants TSP-1 (Recombinant Human Thrombospondin-1, R&D#3074-TH-050, manufactured by R&D Systems, Inc.), PAI-1 (Recombinant Human Serpin E1/PAI-1, R&D#1786-PI-010, manufactured by R&D Systems, Inc.), CCL5 (Recombinant Human CCL5/RANTES, R&D#278-RN-010/CF, manufactured by R&D Systems, Inc.), NRDc (provided by Prof. Eiichiro Nishi, Shiga University of Medical Science), MIF (Recombinant Human MIF, R&D#289-MF-002, manufactured by R&D Systems, Inc.), and IGFBP2 (Recombinant Human IGFBP2, R&D#674-B2-025, manufactured by R&D Systems, Inc.) were added to this basic composition (6F), a medium in which 3 factors of NRDc, MIF, and IGFBP2 were added to the basic composition (3F), a medium in which IGFBP2 was added to the basic composition (IGFBP2), a medium in which MIF was added to the basic composition (MIF), and, a medium in which NRDc was added to the basic composition (NRDc) were prepared. The amount of each factor to be added was 5 ng/mL for MIF and 50 ng/mL for other 5 factors. Cell cultures were carried out using these media from the start of the gene off culture (Day 0) and CD41a/CD42b-positive platelets were counted by FACS on Day 6 from the culture supernatants (FIG. 18, upper drawing). Further, the medium of basic composition (none) was used at the time of starting the gene off culture (Day 0), the cell culture was carried out using a medium to which six factors were added in the same amounts as above without replacing the medium from the start of culture on Day 3 (6 F Day 3), and the platelets were counted on Day 6 by FACS in the same manner (FIG. 18, lower drawing).

Figure 19:
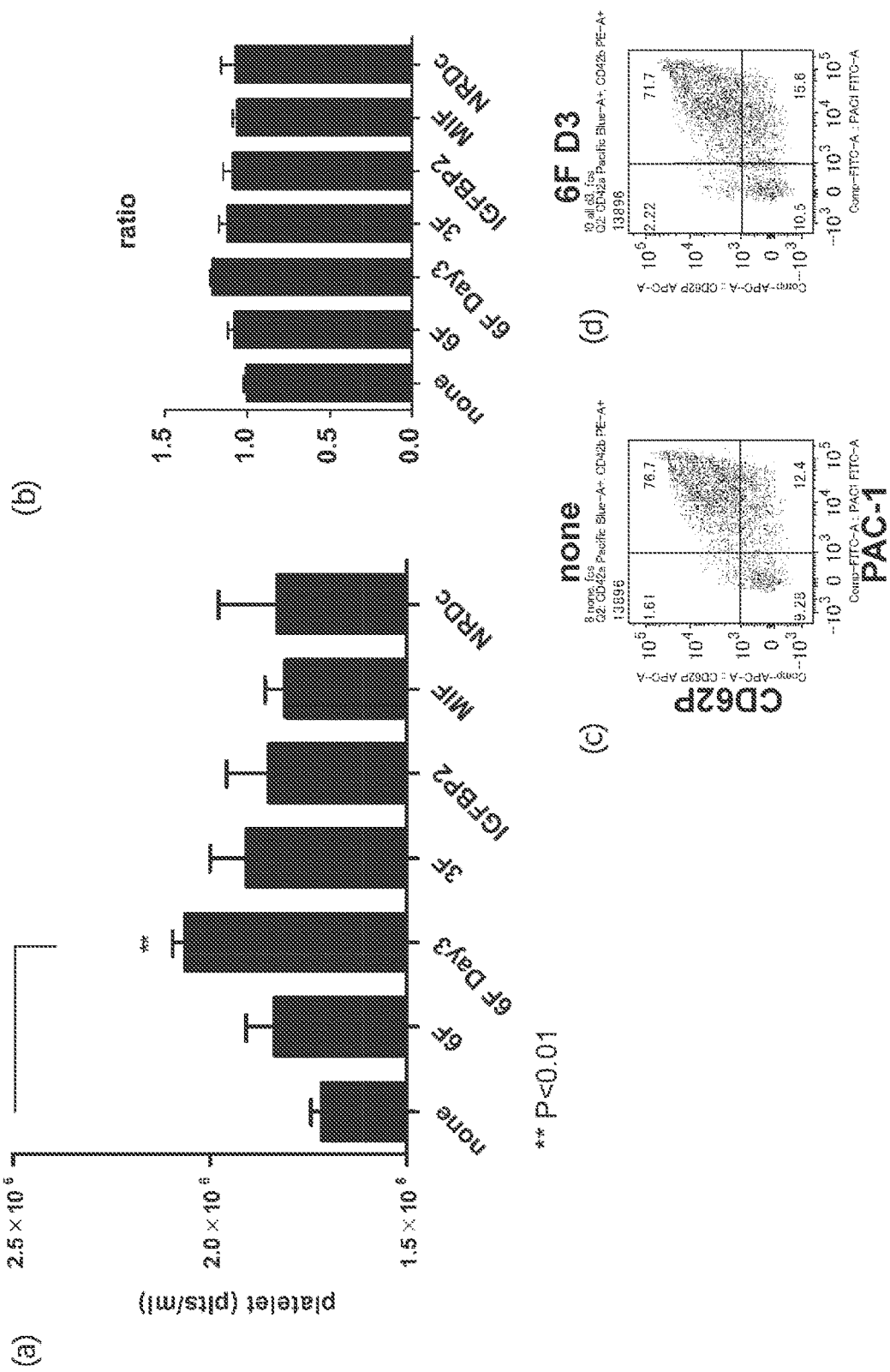
FIG. 19 shows results of the experiments shown in FIG. 18.

The results are shown in FIG. 19. FIG. 19, panel (a) is a graph showing count of CD41a/CD42b-positive platelets, and in the graph the vertical axis represents the number of platelets produced per megakaryocyte and the horizontal axis shows each culture condition. Further, FIG. 19, panel (b), based on the same data, is a graph showing the number of platelets produced under each culture condition in terms of ratios when the number of platelets produced using the medium of basic composition (none) is 1. These results revealed that when six factors were added to the medium of basic composition after 3 days from the start of the off culture (Day 3), a platelet yield was enhanced to about 1.2 times. When these factors were added at the time of starting the off culture (Day 0), effects were small thereby suggesting possible deterioration during 6 days of the culture. Additionally, for none and 6 F Day 3, PAC-1/CD62P-positive platelets were counted. The results are shown in FIG. 19, panels (c) and (d). These results showed that there is no problem in the platelet functions.

Figure 20:
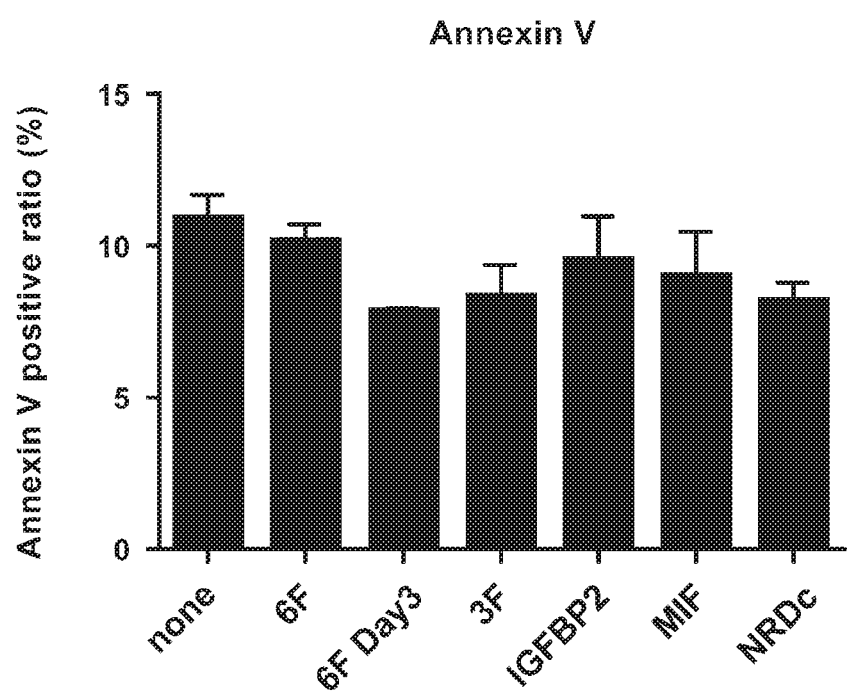
FIG. 20 shows that healthy platelets with a low Annexin V positive ratio can be obtained even when any media shown in FIG. 18 is used.

Further, Annexin V-positive platelets under each culture condition were counted by FACS. The results are shown in FIG. 20. Under any culture condition, healthy platelets having a low Annexin V positive ratio were obtained.

[10. Inhibitory Effect of Histone Deacetylase 6 (HDAC6)]

Figure 21:
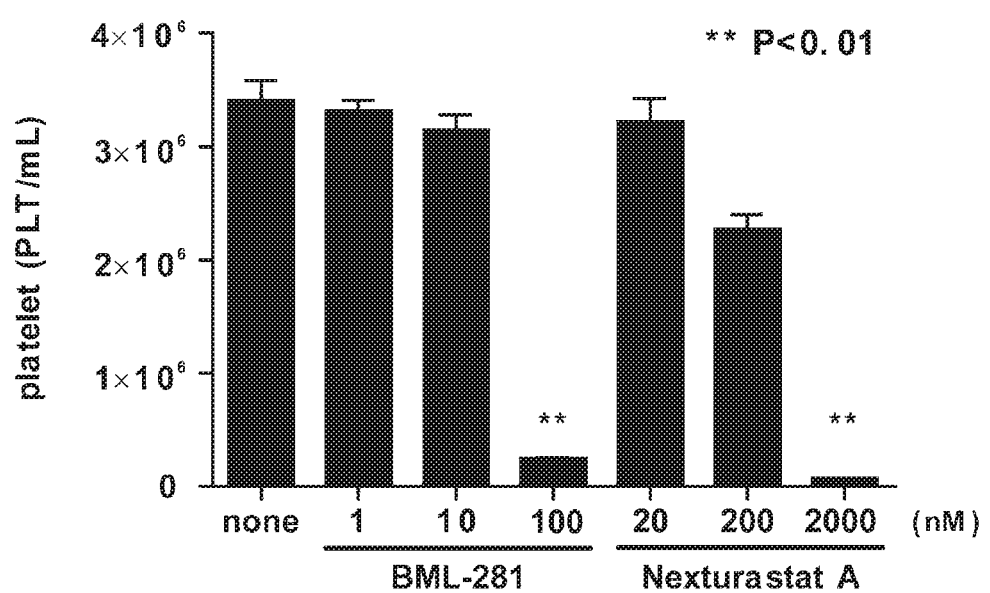
FIG. 21 is a graph showing the number of platelets on Day 6 from HDAC6 inhibitors-BML-281 and Nexturastat A containing media.

After turning genes (c-MYC, BMI1, and BCL-XL) off, $1\times10^5$ cells/ml of imMKCL was seeded in a flask to carry out shaking flask culture using a platelet producing medium. The culture was carried out under the shaking conditions of 100 rpm, 37° C., and 5% $CO_2$. To the platelet producing medium, BML-281 1 nM, 10 nM, or 100 nM, or Nexturastat A 20 nM was added as an HDAC6 inhibitor at the time of starting the culture. BML-281 is known to inhibit HDAC6, 1, 2, 7, 8, and 10, while Nexturastat A is known to specifically inhibit HDAC6. The number of platelets was measured on Day 6 after addition of these HDAC6 inhibitors. The results are shown in FIG. 21. When BML-281 100 nM was added, and when Nexturastat A 2 μM was added, notable reduction in the platelet production was observed.

After turning genes (c-MYC, BMI1, and BCL-XL) off, $1\times10^5$ cells/ml of imMKCL was seeded in a flask to carry out shaking flask culture using a platelet producing medium under a shaking condition of 100 rpm. Further, after turning genes (c-MYC, BMI1, and BCL-XL) off, $1\times10^5$ cells/ml of imMKCL was seeded in a culture dish to carry out static culture. For both shaking culture and static culture, BML-281 100 nM, or Nexturastat A 500 nM, 1 μM, or 2 μM was added at the time of starting the cultures. The number of platelets was measured on Day 6 from addition of these HDAC6 inhibitors. Additionally, Annexin V positive ratios of the obtained platelets were measured. The results of shaking flask culture are shown in FIG. 22. FIG. 22, panel (a) reveals that when Nexturastat A was added as an inhibitor, the number of platelets produced decreases in an inhibitor concentration-dependent manner. Further, FIG. 22, panel (b) reveals that the platelets produced by HDAC6 inhibition had high Annexin V positive ratios indicating poor quality when compared with the platelets obtained by shaking flask culture without addition of the HDAC6 inhibitors. The results of static culture are shown in FIG. 23. FIG. 23, panel (a) reveals that, when Nexturastat A was added as an inhibitor in the static culture, the number of platelets produced decreases in an inhibitor concentration-dependent manner.

FIG. 23, panel (b) confirmed that the platelets produced by the static culture had high Annexin V positive ratios indicating poor quality regardless of the presence or absence of HDAC6 inhibitor addition.

Figure 24:
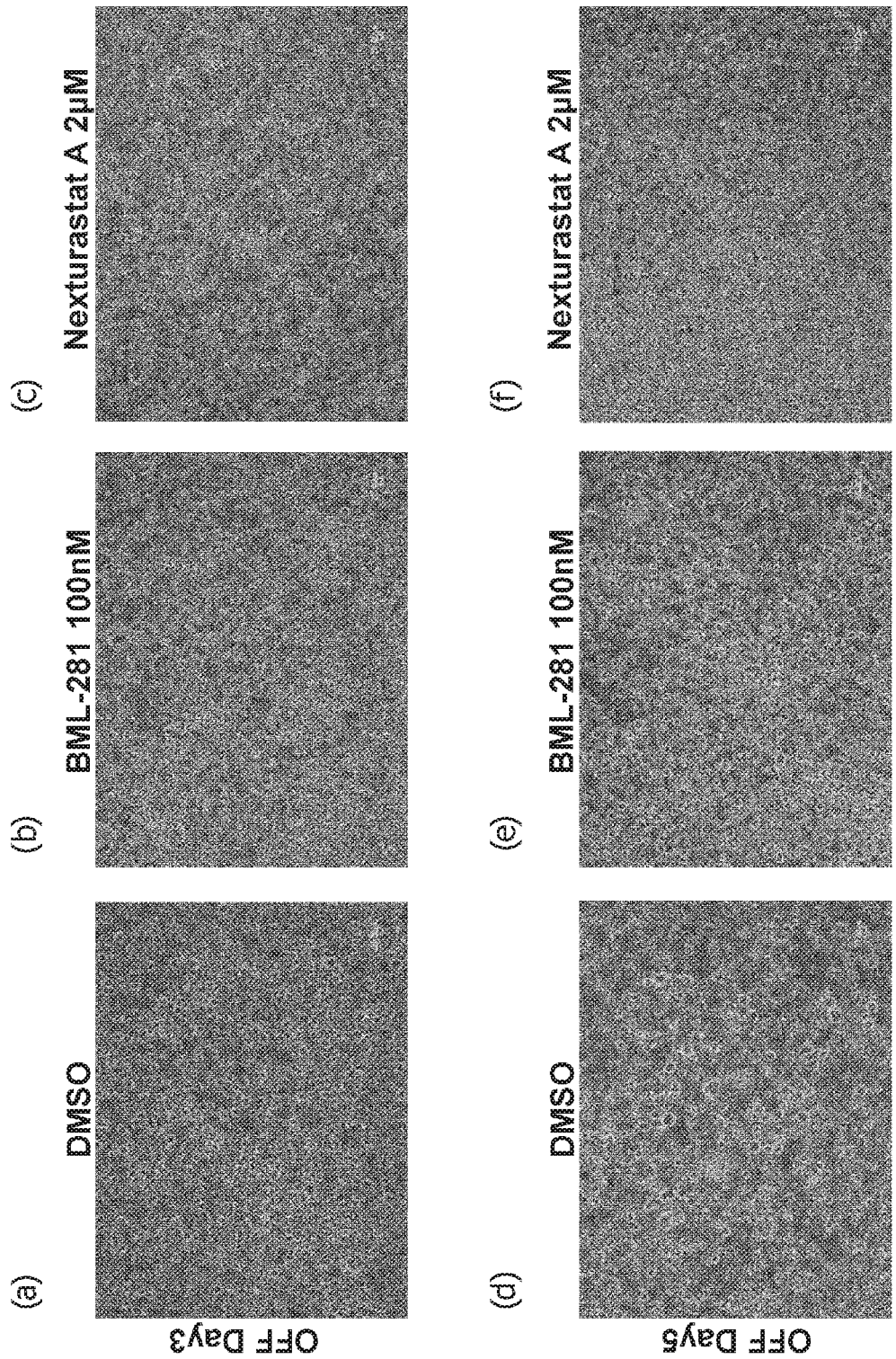
FIG. 24 is a set of microscope photographs showing that megakaryocytes hypertrophy (maturation process) and the platelet production pattern showing the effect of addition of drugs such as DMSO, BML-281, and Nexturastat A on a gene off imMKCL in static culture.

To confirm if apoptosis was caused due to the drug addition, cell morphology was observed when dimethyl sulfoxide (DMSO) was used as a solvent control of the drug or an HDAC6 inhibitor was added at the time of starting the culture in the platelet producing medium in a static culture under the same conditions as above. Microscopic images of the platelets at X20 are shown in FIG. 24. FIG. 24, panel (a) shows cell morphology on Day 3 from the gene off of the static culture to which DMSO was added at a concentration of 0.02%. In the photograph, cell hypertrophy associated with megakaryocyte maturation is observed. FIG. 24, panel (b) shows Day 3 cell morphology from the gene off static culture to which 100 nM of BML-281 was added. Apoptosis is not recognized but cell hypertrophy is recognized. FIG. 24, panel (c) shows cell morphology on Day 3 from the gene off static culture to which Nexturastat A 2 μM was added. Apoptosis was not recognized but cell hypertrophy was observed. In the BML-281 addition group and Nexturastat A addition group, the degree of hypertrophy was slightly lower than the group containing DMSO. FIG. 24, panel (d) shows Day 5 cell morphology from the gene off static culture to which DMSO was added. PPF associated with megakaryocyte maturation is recognized. FIG. 24, panels (e) and (f) show cell morphology on Day 5 from the gene off static culture to which BML-281 100 nM was added and to which Nexturastat A 2 μM was added, respectively. When these HDAC6 inhibitors were added, PPF associated with megakaryocyte maturation was not recognized in both cases. These results revealed that cytotoxicity due to HDAC6 inhibitor addition was not observed. Additionally, when an HDAC6 inhibitor was added, the degree of megakaryocyte maturation is rather hindered but proceeds to hypertrophy. Based on the above findings, HDAC6, seems to have role in the proplatelet formation.

Figure 25:
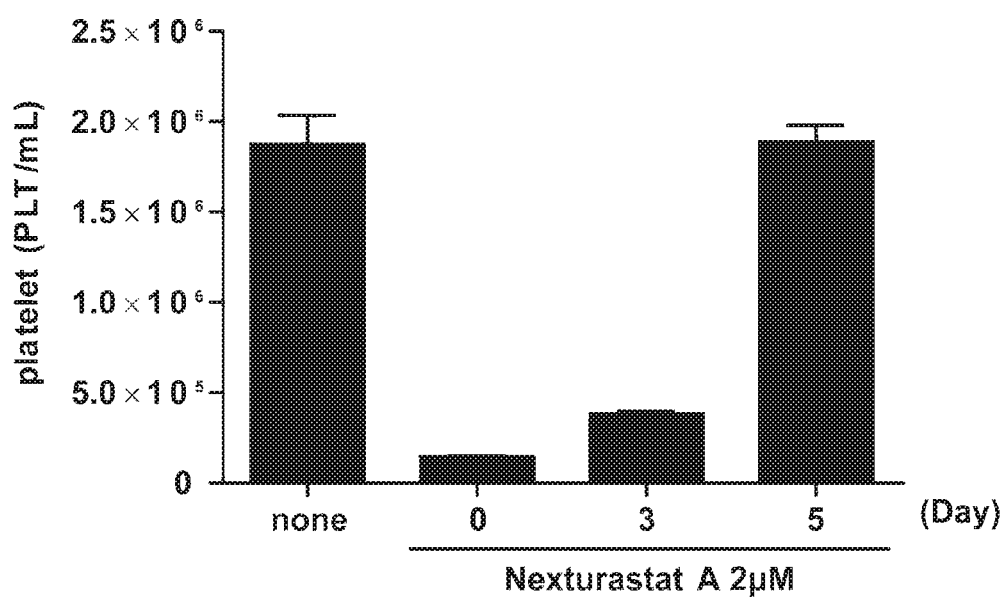
FIG. 25 is a graph showing effects on the amount of platelets produced when the addition of HDAC6 inhibitor were on Day 3 and Day 5 from the start of shaking flask culture (Flask) after the gene off.
Figure 26:
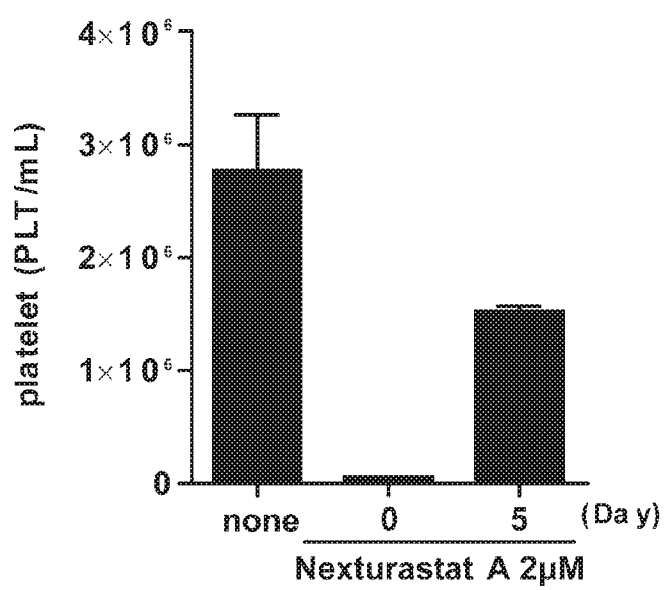
FIG. 26 is a graph showing effects on the amount of platelets produced when the addition of HDAC6 inhibitor were on Day 0 and Day 5 from the start of static culture (Dish) after the gene off.

Subsequently, in order to examine in more detail which process in megakaryocyte maturation is affected by the HDAC6 inhibitor, the timing of adding Nexturastat A 2 μM during the flask culture was changed to Day 3, Day 4, and Day 5 from the start of the culture after the gene off and the effect on the amount of platelets to be produced was studied. Culture conditions other than the timing of adding HDAC6 inhibitors were the same as those in the experiment referring to FIGS. 21 to 24. The results of shaking flask culture are shown in FIG. 25. In the groups in which the drug was added on Day 0 or Days 3 and 4 from the start of the culture after the gene off, notable reduction in the platelet production was recognized. On the other hand, in the group in which the addition was carried out on Day 5, the production equivalent to that in non-addition group was recognized. The results on static culture are shown in FIG. 26. In the shaking flask culture (Flask) shown in FIG. 25, the inhibitory effect by the HDAC6 inhibitor was not recognized in the group in which the addition was carried out on Day 5, whereas in the static culture (Dish), the number of platelets produced reduces about 40% due to the HDAC6 inhibitor. In FIG. 24, panel (c), PPF was recognized at Day 5 in static culture. In view of this, the effect available at the time of shedding platelets (presumed mechanism) seems to be about 40%.

The association of HDAC6 with the megakaryocyte maturation is evident from the study using the inhibitors, however, the mechanism thereof was suggested to be possibly involved with elongation reaction via stabilization of microtube structure because the formation of proplatelets is notably attenuated from the morphology observation results. Further, the platelets produced by the HDAC6 inhibition have high Annexin positive ratios but such a high Annexin positivity is presumably caused by a different mechanism from the static culture in which high Annexin platelets are produced despite the formation of proplatelets.

[11. Impact of MIF and IGFBP2 on Extracellular Matrixes]

Figure 27:
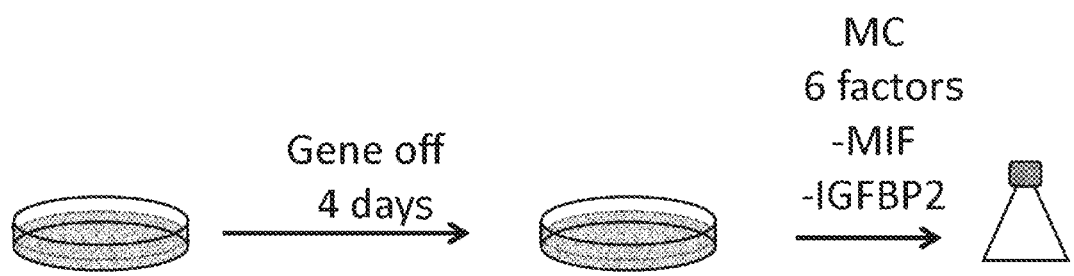
FIG. 27 is a drawing showing an overview of experiment in which cells subjected to static culture for 4 days after the gene off are further subjected to shaking flask culture using a medium in which MIF and IGFBP2 are removed from six factors.
Figure 28:
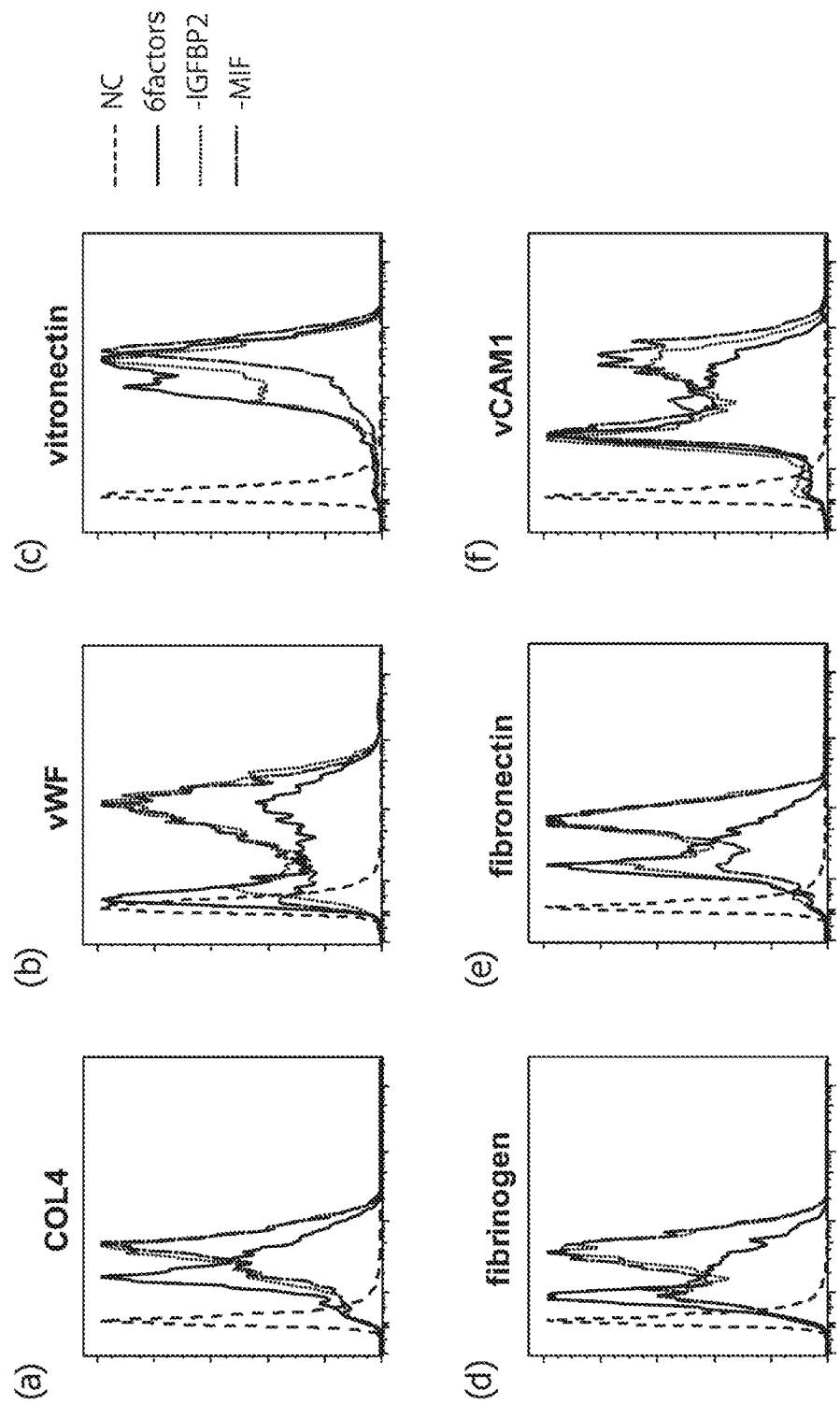
FIG. 28 shows histograms obtained by staining six representative kinds of extracellular matrixes in cells after culturing in flask for one day according to the scheme shown in FIG. 27 and analyzing by FACS. The horizontal axis represents the extracellular matrix content and the vertical axis represents the number of cells. The histogram of type IV collagen (co14) is shown in FIG. 28, panel (a), the histogram of von Willebrand factor (vWF) is shown in FIG. 28, panel (b), the histogram of vitronectin is shown in FIG. 28, panel (c), the histogram of fibrinogen is shown in FIG. 28, panel (d), the histogram of fibronectin is shown in FIG. 28, panel (e), and the histogram of vascular cell adhesion molecule-1 (vCAM1) is shown in FIG. 28, panel (f).

After turning genes (c-MYC, BMI1, and BCL-XL) off, imMKCL was seeded at a concentration of $1\times10^5$ cells/ml in a dish to carry out mature culture for 4 days by static culture using a platelet producing medium. Cells were harvested from this dish and suspended in a medium of each condition (a medium to which six factors were added (6 factors), a medium in which MIF was removed from six factors (–MIF), and a medium in which IGFBP2 was removed from six factors (–IGFBP2)) to carry out shaking flask culture for 1 day. The overview of the experiment is shown in FIG. 27. In FIG. 27, MC refers to Medium Change (MC). The following extracellular matrixes (co14, vWF, vitronectin, fibrinogen, fibronectin, and vCAM1) in cells were stained and analyzed by FACS. FIG. 28 shows histograms of each stained extracellular matrix. The histogram having a peak shifted to the right side of the non-colored (NC) histogram shown with a dotted line shows that the extracellular matrix is not released but remains in the nucleus of the cell. Based on the results of measuring known six kinds of representative extracellular matrixes, it is strongly suggested that MIF and IGFBP2 play an important role in releasing extracellular matrixes to outside the nucleus.

Figure 29:
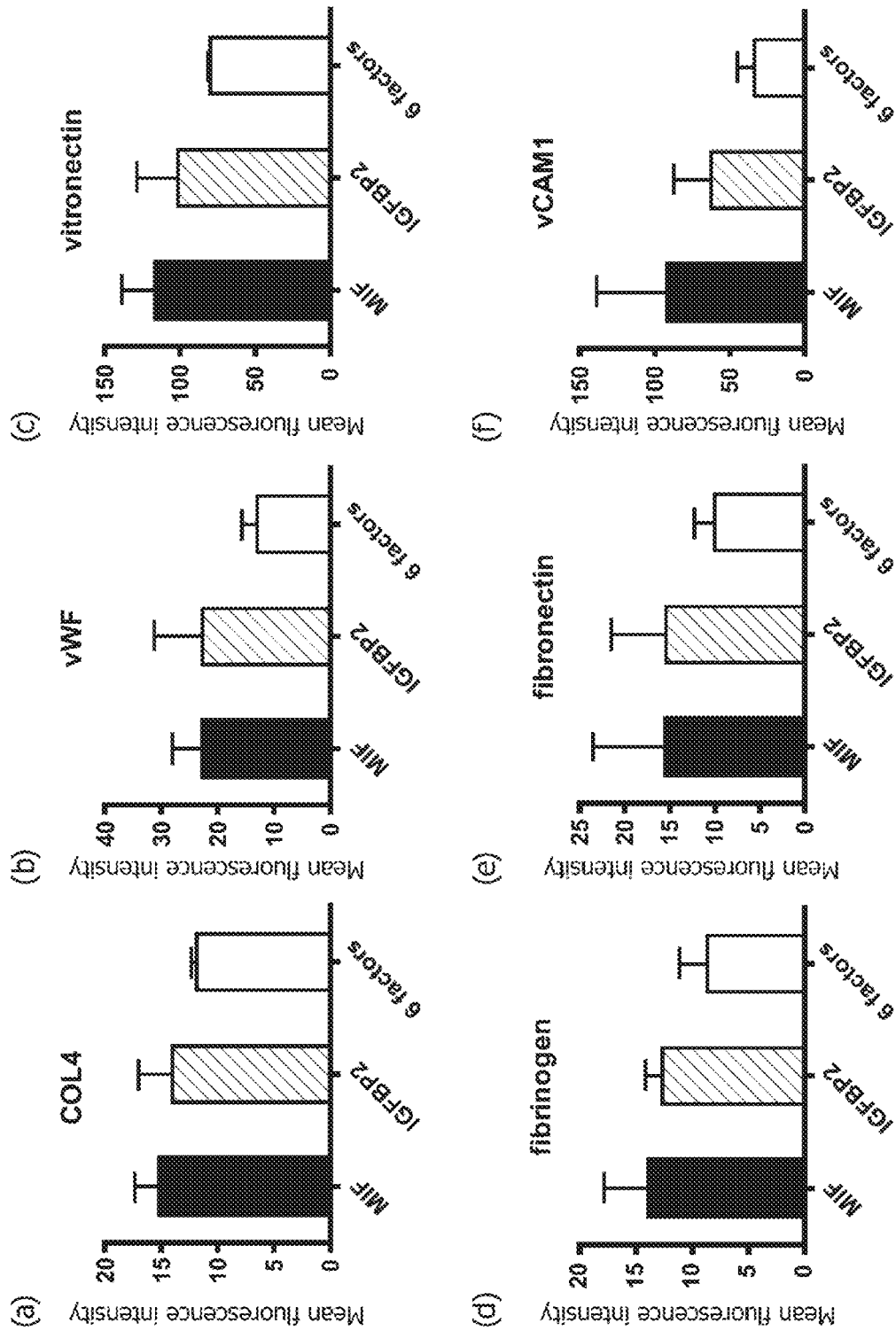
FIG. 29 is a set of graphs showing values obtained by averaging (geo MFI) positive ratios of the total number of cells of extracellular matrixes and correcting the averaged value with non-colored (NC) matrix.

FIG. 29 shows values obtained by averaging (geo MFI) positive ratios of the total number of cells of extracellular matrixes based on the histograms of FIG. 28 and correcting with non-colored (NC) matrix. The results revealed that, in the groups of 6 factors -MIF and 6 factors -IGFBP2, mean fluorescence intensity (MFI) is higher than that in the six factors group. In other words, it is suggested that extracellular matrixes are released when six factors are added and mechanical stress is applied to medium. Additionally, it was suggested that MIF and IGFBP2 are involved with the release of extracellular matrixes.

[12. Behavior Confirmation of Proteins by Immunostaining]

Figure 30:
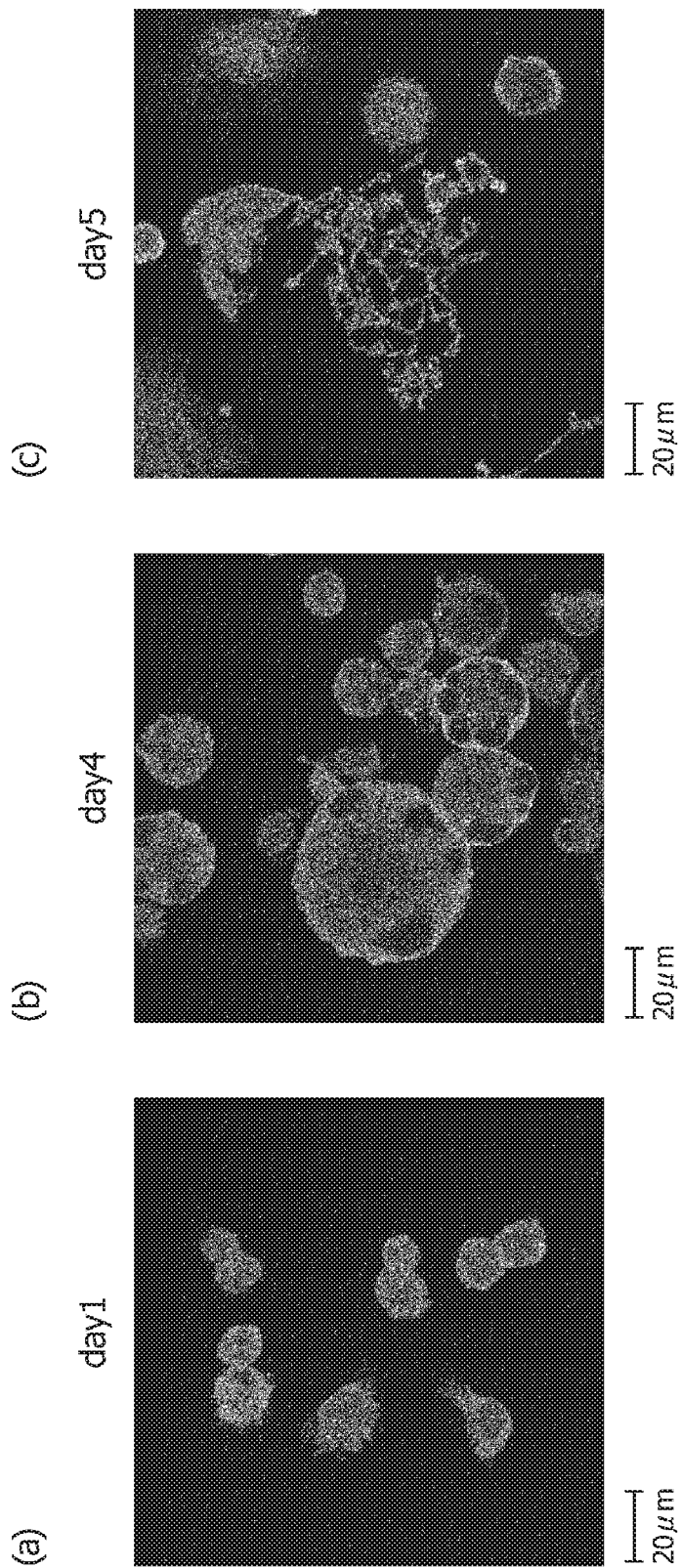
FIG. 30 shows fluorescence microscope photographs of imMKCL after turning off the genes (c-MYC, BMI1, and BCL-XL) and culturing in a platelet producing media for 1 to 5 days on a slide glass coated with fibronectin, and immunostaining the cells on Day 1, Day 4, and Day 5 with NRDc (red) and HDAC6 (green).

After turning genes (c-MYC, BMI1, and BCL-XL) off, imMKCL was cultured for 1 to 5 days on a slide glass coated with fibronectin using a platelet producing medium. Cells on Day 1, Day 4, and Day 5 were fixed on slide glasses, immunostained with an anti-NRDc antibody and an anti-HDAC6 antibody, and subsequently observed using a fluorescence microscope. The results are shown in FIG. 30. HDAC6 was present locally in the cytoplasm on all Day 1, Day 4, and Day 5 samples. NRDc was present locally in the nucleus and cytoplasm on Day 1, present locally in the vicinity of cell membrane on Day 4, and present locally in the cytoplasm on Day 5. The results of immunostaining suggested that the local presences of NRDc and HDAC6 in the imMKCL maturation phase substantially match.

[13. Detection of Interaction Between NRDc and HDAC6]

Figure 31:
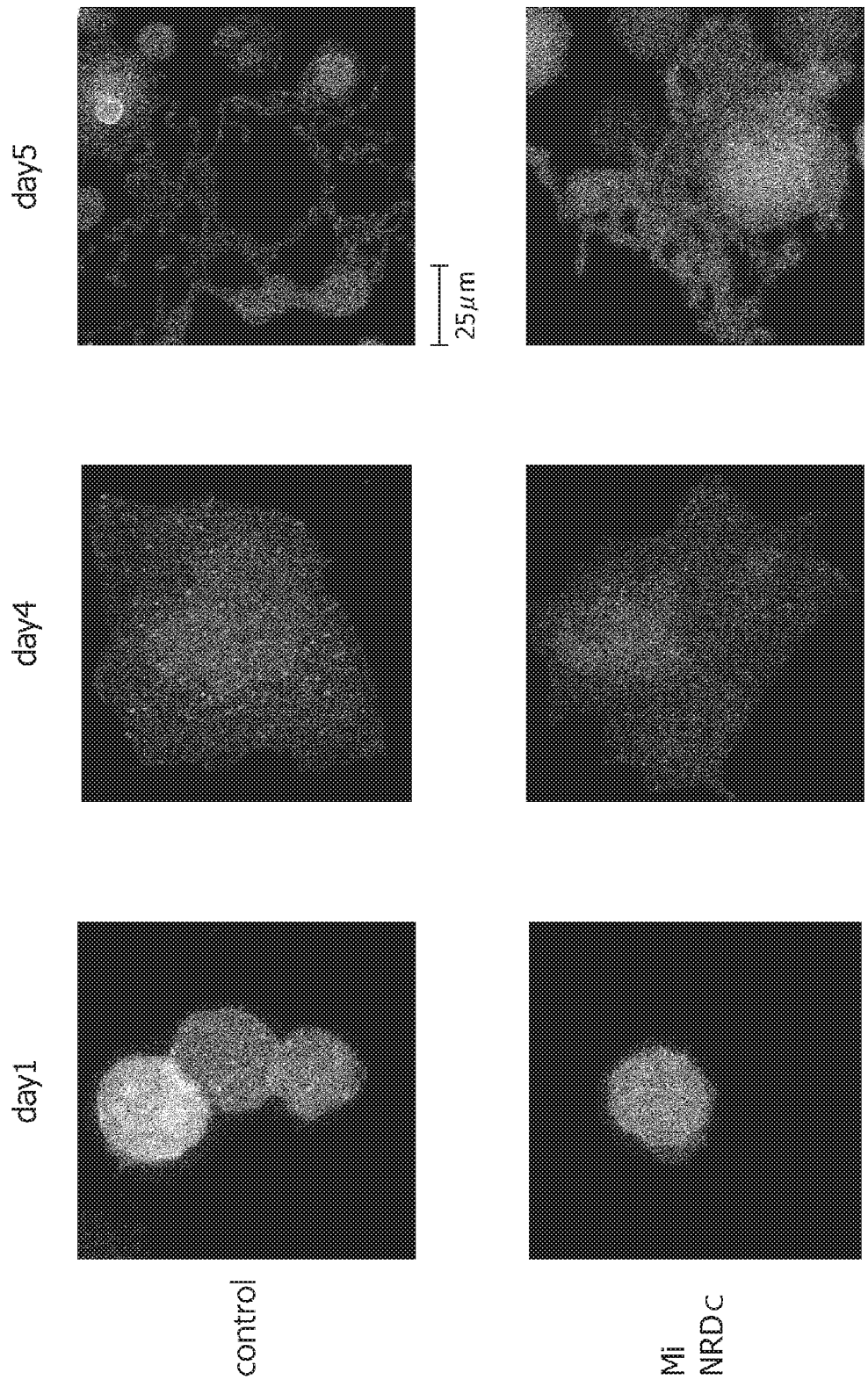
FIG. 31 is a set of fluorescence microscope photographs showing results of proximity ligation assay using Duolink (Registered trade mark) PLA. The assay shows the interaction between NRDc and HDAC6. After the gene is switched off, it was shown that NRDc and HDAC6 interact (red dots) on Day 1, Day 4, and Day 5 (control). In the imMKCL with suppressed expression of NRDc (MiNRDc), a decrease in the interaction sites between NRDc and HDAC6 is shown.
Figure 32:
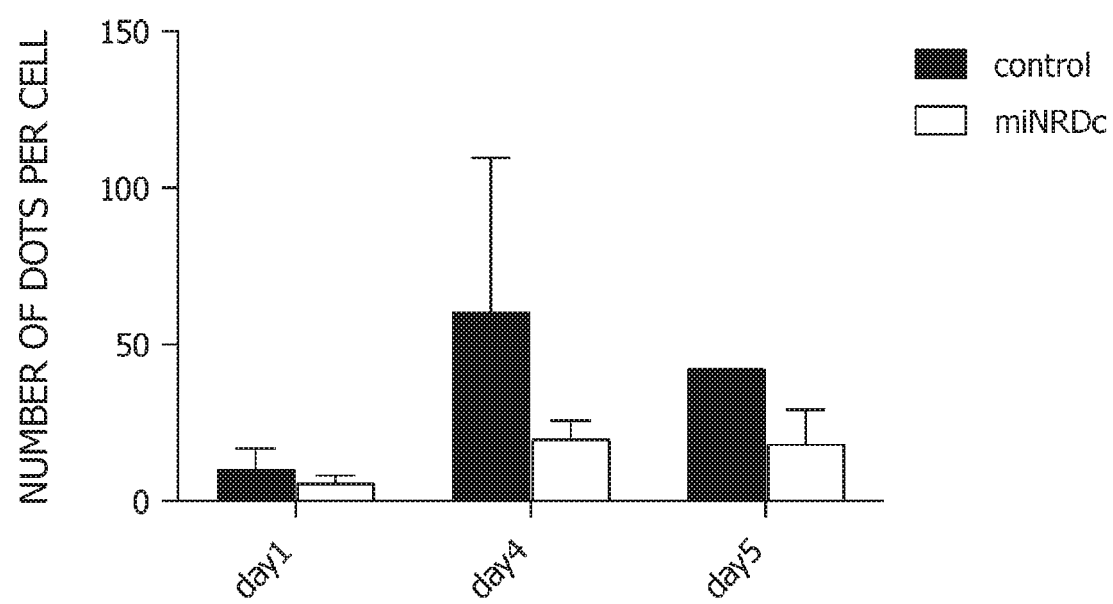
FIG. 32 is a graph showing the number of interaction sites between NRDc and HDAC6 per cell on Day 1, Day 4, and Day 5 after the gene is switched off.

Subsequently, the interaction between NRDc and HDAC6 was verified using Duolink (Registered trade mark) PLA (manufactured by Sigma-Aldrich). FIG. 31 is a set of fluorescence microscope photographs showing the results of proximity ligation assay by Duolink (Registered trade mark) PLA. After turning genes (c-MYC, BMI1, and BCL-XL) off, the interaction (red dots) between NRDc and HDAC6 was shown (control) on Day 1, Day 4, and Day 5. It was shown that, in imMKCL (miNRDc) in which the expression of NRDc was suppressed (knockdown) using RNA interferometry, the interaction sites between NRDc and HDAC6 decreased. Further, for each of the control and miNRDc, the number of interaction sites (red dots) between NRDc and HDAC6 per cell was counted on Day 1, Day 4, and Day 5 after the gene is turned off. The results are shown in FIG. 32. It was shown that, in miNRDc, the interaction sites between NRDc and HDAC6 decrease when compared with the control. Further, it was revealed that the control and miNRDc both had the largest number of interaction sites between NRDc and HDAC6 on Day 4. This finding is correlated well with the effect of HDAC6 inhibitors which lasts up to Day 4.

The invention claimed is:

1. A method for producing platelets, comprising the steps of:
   (1) culturing megakaryocytes in a platelet producing medium, and
   (2) harvesting platelets obtained by the culturing;
   wherein the step of culturing comprises:
   (a) promoting a release of one or more platelet production promoting factor(s), wherein the factor(s) comprise MIF, NRDc, IGFBP2, TSP-1, PAI-1, or CCL5, from megakaryocytes by applying mechanical stress including turbulence by vortex; and/or
   (b) externally adding platelet production promoting factors including MIF, NRDc, and IGFBP2,
   wherein the step of culturing comprises step (b) and wherein step (b) further comprises externally adding at least one platelet production promoting factor(s) comprising TSP-1, PAI-1, or CCL5.

2. The method according to claim 1, wherein the step of culturing comprises step (a).

3. The method according to claim 2, wherein the one or more platelet production promoting factor(s) of step (a) comprise MIF, NRDc, IGFBP2, TSP-1, or PAI-1.

4. The method according to claim 2, wherein step (a) comprises promoting release of platelet production promoting factors including MIF, NRDc, IGFBP2, TSP-1, PAI-1, and CCL5.

5. The method according to claim 1, wherein step (b) comprises externally adding platelet production promoting factors TSP-1, PAI-1, and CCL5.

6. The method according to claim 1, wherein step (b) is carried out 1 to 3 days before the harvesting.

7. The method according to claim 1, wherein the step of culturing further comprises controlling activity of histone deacetylase 6.

8. The method according to claim 1, further comprising forcibly expressing an oncogene, a polycomb gene, and an apoptosis suppressor gene in cells more undifferentiated than megakaryocytes to obtain immortalized megakaryocytes before step (1).

* * * * *

UNITED STATES PATENT AND TRADEMARK OFFICE
CERTIFICATE OF CORRECTION

PATENT NO. : 11,952,587 B2
APPLICATION NO. : 16/491219
DATED : April 9, 2024
INVENTOR(S) : Eto et al.

It is certified that error appears in the above-identified patent and that said Letters Patent is hereby corrected as shown below:

In the Specification

Column 9, Line 48-49: Please correct "-cyclohexanecarboxamide 2HCl·$H_2O$" to read
-- -cyclohexanecarboxamide·2HCl·$H_2O$--

Column 12, Line 21: Please correct "$NRD_c$" to read --NRDc--

Column 16, Line 9: Please correct "Mitochondria, a" to read --Mitochondria, α--

Column 22, Lines 3-4: Please delete the paragraph break between "manner." and "FIG. 23"

Column 24, Lines 7-8: Please delete the paragraph break between "expression of" and "NRDc"

Signed and Sealed this
Thirtieth Day of July, 2024

Katherine Kelly Vidal
*Director of the United States Patent and Trademark Office*